(12) United States Patent
Barket, Jr. et al.

(10) Patent No.: US 9,347,920 B2
(45) Date of Patent: *May 24, 2016

(54) ANALYTICAL INSTRUMENTS, ASSEMBLIES, AND METHODS

(71) Applicant: FLIR DETECTION, INC., Stillwater, OK (US)

(72) Inventors: Dennis Barket, Jr., Lafayette, IN (US); Garth E. Patterson, Jefferson, MD (US); Mark Gregory, Lafayette, IN (US); Jason Springston, Carmel, IN (US)

(73) Assignee: FLIR DETECTION, INC., Stillwater, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/617,258

(22) Filed: Feb. 9, 2015

(65) Prior Publication Data

US 2015/0177201 A1 Jun. 25, 2015

Related U.S. Application Data

(63) Continuation of application No. 12/981,024, filed on Dec. 29, 2010, now Pat. No. 8,952,321, which is a
(Continued)

(51) Int. Cl.
*H01J 49/00* (2006.01)
*G01N 30/72* (2006.01)
(Continued)

(52) U.S. Cl.
CPC .............. *G01N 30/7206* (2013.01); *G01N 30/06* (2013.01); *H01J 49/0022* (2013.01); *H01J 49/02* (2013.01); *G01N 1/405* (2013.01); *G01N 30/722* (2013.01); *G01N 2035/00326* (2013.01)

(58) Field of Classification Search
CPC .............. H01J 49/0022; H01J 49/0013; H01J 49/0095; G01N 2030/025; G01N 30/72; G01N 30/88
USPC .......................... 250/281, 282, 288, 289, 290
See application file for complete search history.

(56) References Cited

U.S. PATENT DOCUMENTS 3,633,173 A 1/1972 Edge
3,984,692 A 10/1976 Arsenault
(Continued)

FOREIGN PATENT DOCUMENTS

CN 1068656 2/1993
DE 4008388 9/1991
(Continued)

OTHER PUBLICATIONS

EP 03812512 Supp Search Report, Jan. 26, 2007, Griffin Analytical Tech.
(Continued)

*Primary Examiner* — Michael Maskell
(74) *Attorney, Agent, or Firm* — Wells St. John P.S.

(57) ABSTRACT

Person-portable mass analysis instrumentation configured to perform multidimensional mass analysis is provided. Mass analysis instrumentation can include a housing encompassing components of the instrumentation with the housing of the instrumentation defining a space having a volume of equal to or less than about 100,000 cm$^3$. Instrument assemblies are also provided that can include a housing coupled to an instrument component isolation assembly, wherein the component isolation assembly is isolated from an environment exterior to the housing. Exemplary instrument assemblies can include at least first and second components configured to provide analysis with a housing of the instrument at least partially encompassing the first and second components and the first component being rigidly affixed to the housing. An isolation assembly can also be provided that is rigidly affixed to the second component with the isolation assembly being isolated from received inputs of the housing.

18 Claims, 15 Drawing Sheets

Related U.S. Application Data continuation of application No. 11/629,953, filed as application No. PCT/US2005/020783 on Jun. 13, 2005, now abandoned.

(60) Provisional application No. 60/580,144, filed on Jun. 15, 2004, provisional application No. 60/580,582, filed on Jun. 16, 2004.

(51) Int. Cl.
  *H01J 49/02* (2006.01)
  *G01N 30/06* (2006.01)
  *G01N 1/40* (2006.01)
  *G01N 35/00* (2006.01)

(56) References Cited

U.S. PATENT DOCUMENTS

| | | | |
|---|---|---|---|
| 3,992,632 A | 11/1976 | Kruger et al. | |
| 4,008,388 A | 2/1977 | McLafferty et al. | |
| 4,105,916 A | 8/1978 | Siegel | |
| 4,388,531 A | 6/1983 | Stafford et al. | |
| 4,423,324 A | 12/1983 | Stafford et al. | |
| 4,433,982 A | 2/1984 | Odernheimer et al. | |
| 4,540,884 A | 9/1985 | Stafford et al. | |
| 4,567,897 A | 2/1986 | Endo et al. | |
| 4,644,494 A | 2/1987 | Muller | |
| 4,755,685 A | 7/1988 | Kawanami et al. | |
| 4,757,198 A * | 7/1988 | Korte et al. | 250/288 |
| 4,761,545 A | 8/1988 | Marshall et al. | |
| 4,766,312 A | 8/1988 | Fergusson et al. | |
| 4,771,172 A | 9/1988 | Weber-Grabau et al. | |
| 4,791,292 A * | 12/1988 | Cooks et al. | 250/288 |
| 4,810,882 A | 3/1989 | Bateman | |
| 4,849,628 A | 7/1989 | McLuckey et al. | |
| 4,882,484 A | 11/1989 | Franzen et al. | |
| 4,912,326 A | 3/1990 | Naito | |
| 4,945,236 A | 7/1990 | Mogami et al. | |
| 4,956,788 A | 9/1990 | Guan et al. | |
| 4,988,867 A | 1/1991 | Laprade | |
| 4,991,428 A | 2/1991 | Heyde | |
| 4,996,422 A | 2/1991 | Mitsui et al. | |
| 5,015,848 A | 5/1991 | Bomse et al. | |
| 5,083,021 A * | 1/1992 | Devant et al. | 250/292 |
| 5,083,450 A | 1/1992 | Grindstaff | |
| 5,107,109 A | 4/1992 | Stafford, Jr. et al. | |
| 5,109,691 A | 5/1992 | Corrigan et al. | |
| 5,153,433 A | 10/1992 | Andresen et al. | |
| 5,155,357 A | 10/1992 | Hemond | |
| 5,202,561 A | 4/1993 | Giessmann et al. | |
| 5,245,192 A | 9/1993 | Houseman | |
| 5,248,882 A | 9/1993 | Liang | |
| 5,304,799 A | 4/1994 | Kurzweg | |
| 5,313,061 A * | 5/1994 | Drew et al. | 250/281 |
| 5,324,939 A | 6/1994 | Louris et al. | |
| 5,345,809 A * | 9/1994 | Corrigan et al. | 73/23.2 |
| 5,401,965 A | 3/1995 | Kaneko et al. | |
| 5,420,425 A | 5/1995 | Bier et al. | |
| 5,426,300 A | 6/1995 | Voss et al. | |
| 5,436,447 A | 7/1995 | Shew | |
| 5,448,061 A | 9/1995 | Wells | |
| 5,448,062 A | 9/1995 | Cooks et al. | |
| 5,462,660 A | 10/1995 | Singleton et al. | |
| 5,479,012 A | 12/1995 | Wells | |
| 5,481,107 A | 1/1996 | Takada et al. | |
| 5,509,602 A | 4/1996 | Liu | |
| 5,525,799 A | 6/1996 | Andresen et al. | |
| 5,559,325 A | 9/1996 | Franzen et al. | |
| 5,572,022 A | 11/1996 | Schwartz et al. | |
| 5,686,655 A | 11/1997 | Itoi | |
| 5,696,376 A | 12/1997 | Doroshenko et al. | |
| 5,723,862 A | 3/1998 | Forman | |
| 5,760,785 A | 6/1998 | Barber et al. | |
| 5,773,822 A | 6/1998 | Kitamura et al. | |
| 5,777,205 A | 7/1998 | Nakagawa et al. | |
| 5,789,747 A | 8/1998 | Kato et al. | |
| 5,808,308 A | 9/1998 | Holkeboer | |
| 5,818,055 A | 10/1998 | Franzen | |
| 5,837,883 A | 11/1998 | Itoi | |
| 5,844,237 A | 12/1998 | Whitehouse et al. | |
| 5,852,295 A | 12/1998 | Da Silveira et al. | |
| 5,896,196 A | 4/1999 | Pinnaduwage | |
| 6,025,590 A | 2/2000 | Itoi | |
| 6,107,623 A | 8/2000 | Bateman | |
| 6,133,568 A | 10/2000 | Weiss et al. | |
| 6,165,251 A | 12/2000 | Lemieux et al. | |
| 6,215,146 B1 | 4/2001 | Umeda et al. | |
| 6,235,197 B1 | 5/2001 | Anderson et al. | |
| 6,239,429 B1 | 5/2001 | Blessing et al. | |
| 6,253,162 B1 | 6/2001 | Jarman et al. | |
| 6,287,988 B1 | 9/2001 | Nagamine et al. | |
| 6,329,654 B1 | 12/2001 | Gulcicek et al. | |
| 6,351,983 B1 * | 3/2002 | Haas et al. | 73/23.37 |
| 6,410,914 B1 | 6/2002 | Park et al. | |
| 6,469,298 B1 | 10/2002 | Ramsey et al. | |
| 6,472,661 B1 | 10/2002 | Tanaka et al. | |
| 6,472,664 B1 | 10/2002 | Kyushima et al. | |
| 6,476,537 B1 | 11/2002 | Pease et al. | |
| 6,487,523 B2 | 11/2002 | Jarman et al. | |
| 6,489,610 B1 | 12/2002 | Barofsky et al. | |
| 6,489,649 B2 | 12/2002 | Kobayashi et al. | |
| 6,496,905 B1 | 12/2002 | Yoshioka et al. | |
| 6,507,019 B2 | 1/2003 | Chernushevich et al. | |
| 6,509,602 B2 | 1/2003 | Yamazaki et al. | |
| 6,530,563 B1 * | 3/2003 | Miller et al. | 267/136 |
| 6,541,765 B1 | 4/2003 | Vestal | |
| 6,541,768 B2 | 4/2003 | Andrien et al. | |
| 6,549,861 B1 | 4/2003 | Mark et al. | |
| 6,559,443 B2 | 5/2003 | Shiokawa et al. | |
| 6,570,151 B1 | 5/2003 | Grosshans et al. | |
| 6,577,531 B2 | 6/2003 | Kato | |
| 6,586,727 B2 | 7/2003 | Bateman et al. | |
| 6,593,568 B1 | 7/2003 | Whitehouse et al. | |
| 6,593,585 B1 | 7/2003 | Loopstra et al. | |
| 6,596,585 B2 | 7/2003 | Kobayashi et al. | |
| 6,596,989 B2 | 7/2003 | Kato | |
| 6,621,077 B1 | 9/2003 | Geuvremont et al. | |
| 6,646,254 B2 | 11/2003 | Tanaka | |
| 6,649,129 B1 | 11/2003 | Neal | |
| 6,674,067 B2 | 1/2004 | Grosshans et al. | |
| 6,677,582 B2 | 1/2004 | Yamada et al. | |
| 6,679,093 B2 | 1/2004 | Johnson et al. | |
| 6,686,592 B1 | 2/2004 | Sakairi et al. | |
| 6,710,336 B2 | 3/2004 | Wells | |
| 6,717,130 B2 | 4/2004 | Bateman et al. | |
| 6,737,644 B2 | 5/2004 | Itoi | |
| 6,744,045 B2 * | 6/2004 | Fries et al. | 250/288 |
| 6,750,449 B2 | 6/2004 | Marcus | |
| 6,753,523 B1 | 6/2004 | Whitehouse et al. | |
| 6,756,640 B2 | 6/2004 | Yamazaki et al. | |
| 6,759,652 B2 | 7/2004 | Yoshinari et al. | |
| 6,759,706 B2 | 7/2004 | Kobayashi | |
| 6,762,406 B2 | 7/2004 | Cooks et al. | |
| 6,764,902 B2 | 7/2004 | Kobayashi et al. | |
| 6,815,673 B2 | 11/2004 | Plomley et al. | |
| 6,825,466 B2 | 11/2004 | Mordekhay | |
| 6,835,927 B2 | 12/2004 | Becker et al. | |
| 6,861,650 B2 | 3/2005 | Kondo et al. | |
| 6,888,130 B1 * | 5/2005 | Gonin | 250/287 |
| 6,902,937 B2 | 6/2005 | Vanatta | |
| 6,906,322 B2 | 6/2005 | Berggren et al. | |
| 6,939,718 B2 | 9/2005 | Singh et al. | |
| 7,015,466 B2 | 3/2006 | Takats et al. | |
| 7,026,177 B2 | 4/2006 | Laprade | |
| 7,045,776 B2 | 5/2006 | Kaufman et al. | |
| 7,047,144 B2 | 5/2006 | Steiner | |
| 7,129,481 B2 | 10/2006 | Overney | |
| 7,138,626 B1 | 11/2006 | Karpetsky | |
| 7,230,601 B2 | 6/2007 | Yamazaki et al. | |
| 7,294,832 B2 | 11/2007 | Wells et al. | |
| 7,339,820 B2 | 3/2008 | Kato | |
| 7,355,169 B2 | 4/2008 | McLuckey et al. | |
| 7,388,197 B2 | 6/2008 | McLean et al. | |
| 7,399,415 B2 | 7/2008 | Srinivasan et al. | |

(56) References Cited

U.S. PATENT DOCUMENTS

| | | |
|---|---|---|
| 7,427,750 B2 | 9/2008 | Grossenbacher |
| 7,439,121 B2 | 10/2008 | Ohmi et al. |
| 7,449,170 B2 | 11/2008 | Regnier et al. |
| 7,462,821 B2 * | 12/2008 | Barket et al. ............... 250/288 |
| 7,735,352 B2 | 6/2010 | Alm et al. |
| 2002/0005479 A1 | 1/2002 | Yoshinari et al. |
| 2002/0113268 A1 | 8/2002 | Koyama et al. |
| 2002/0195556 A1 | 12/2002 | Yoshinari et al. |
| 2003/0089846 A1 * | 5/2003 | Cooks et al. ............... 250/281 |
| 2003/0113936 A1 | 6/2003 | Yamamoto |
| 2003/0155502 A1 * | 8/2003 | Grosshans et al. ............ 250/282 |
| 2004/0172200 A1 | 9/2004 | Kearney et al. |
| 2005/0272168 A1 | 12/2005 | Zhang et al. |
| 2006/0016979 A1 | 1/2006 | Yang et al. |
| 2006/0231769 A1 | 10/2006 | Stresau et al. |
| 2006/0255258 A1 | 11/2006 | Wang et al. |
| 2007/0162232 A1 | 7/2007 | Patterson |
| 2007/0213940 A1 | 9/2007 | Rardin |

FOREIGN PATENT DOCUMENTS

| | | |
|---|---|---|
| EP | 0336990 | 10/1989 |
| EP | 0476062 | 8/1996 |
| GB | 2 026 231 | 8/1979 |
| GB | 2 363 249 | 12/2001 |
| GB | 2 406 434 | 3/2005 |
| JP | 63-318061 | 12/1988 |
| JP | 11-073911 | 3/1999 |
| JP | 2000-314724 | 11/2000 |
| WO | WO 01/22079 | 3/2001 |
| WO | WO 01/93307 | 12/2001 |
| WO | WO 2004/097352 | 11/2004 |
| WO | PCT/US04/001144 | 7/2005 |
| WO | PCT/US04/12849 | 10/2005 |
| WO | PCT/US04/29029 | 3/2006 |
| WO | PCT/US04/29127 | 3/2006 |
| WO | PCT/US05/20783 | 12/2006 |
| WO | PCT/US04/29028 | 2/2007 |
| WO | PCT/US06/15948 | 10/2007 |

OTHER PUBLICATIONS

EP 047506803 Supp Search Rept., Apr. 18, 2008, Griffin Analytical Tech.
WO PCT/US03/38587 Search Report, Aug. 10, 2004, Griffin Analytical Tech.
WO PCT/US04/001144 Search Report, Apr. 6, 2005, Griffin Analytical Tech.
WO PCT/US04/001144 WrittenOpinion, Apr. 6, 2005, Griffin Analytical Tech.
WO PCT/US04/12849 Search Report, Jun. 23, 2005, Griffin Analytical Tech.
WO PCT/US04/12849 Written Opinion, Jun. 23, 2005, Griffin Analytical Tech.
WO PCT/US04/29028 Search Report, Jan. 26, 2007, Griffin Analytical Tech.
WO PCT/US04/29028 Written Opinion, Jan. 26, 2007, Griffin Analytical Tech.
WO PCT/US04/29029 Search Report, Sep. 9, 2005, Griffin Analytical Tech.
WO PCT/US04/29029 Written Opinion, Sep. 9, 2005, Griffin Analytical Tech.
WO PCT/US04/29127 Search Report, Jul. 18, 2005, Griffin Analytical Tech.
WO PCT/US04/29127 Written Opinion, Jul. 18, 2005, Griffin Analytical Tech.
WO PCT/US05/20783 Search Report, Dec. 16, 2005, Griffin Analytical Tech.
WO PCT/US05/20783 Written Opinion, Dec. 16, 2005, Griffin Analytical Tech.
WO PCT/US06/15948 Search Report, Feb. 27, 2007, Griffin Analytical Tech.
WO PCT/US06/15948 Written Opinion, Feb. 27, 2007, Griffin Analytical Tech.
Badman et al., "Cylindrical Ion Trap Array with Mass Selection by Variation in Trap Dimensions", Analytical Chemistry vol. 72, No. 20, Oct. 15, 2000, United States, pp. 5079-5096.
Barlow et al., "Determination of Analytic Potentials from Finite Element Computations", International Journal of Mass Spectrometry 207, 2001, Netherlands, pp. 19-29.
Bollen et al., "ISOLTRAP: A Tandem Penning Trap System for Accurate On-line Mass Determination of Short-Lived Isotopes", Nuclear Instruments and Methods in Physics Research A vol. 368, 1996, Netherlands, pp. 675-697.
Camel et al., "Trace Enrichment Methods for the Determination of Organic Pollutants in Ambient Air", Journal of Chromatography A., 710, 1995, Netherlands, pp. 3-19.
Carroll et al., "A Dual Vacuum Chamber Fourier Transform Mass Spectrometer with Rapidly Interchangeable LSIMS and MALDI, and ESI Sources: Initial Results with LSIMS and MALDI", Analytical Chemistry vol. 68, No. 10, May 15, 1996, United States, pp. 1798-1804.
de Hoffmann. "Tandem Mass Spectrometry: A Primer", Journal of Mass Spectrometry vol. 31, 1996, United Kingdom, pp. 129-137.
Groves, "Field Portable MS for Explosive Detection", 4th Harsh Environments Mass Spectrometry Workshop, Oct. 9, 2003, United Kingdom, all slides (31 pages).
Jardine et al., "A Tandem Time-of-Flight Mass Spectrometer", Organic Mass Spectrometry vol. 27, 1992, United Kingdom, pp. 1077-1083.
Johnson et al., "Membrane Introduction Mass Spectrometry: Trends and Applications", Mass Spectrometry Reviews vol. 19, 2000, United States, pp. 1-37.
Louris et al., "Instrumentation, Applications, and Energy Deposition in Quadrupole Ion-Trap Tandem Mass Spectrometry", Analytical Chemistry vol. 59, 1987, United States, pp. 1677-1685.
McLuckey et al., "High Explosives Vapor Detection by Glow Discharge—Ion Trap Mass Spectrometry", Rapid Communications in Mass Spectrometry vol. 10, 1996, United Kingdom, pp. 287-298.
Ojala, "Novel Membrane Inlet mass Spectrometic Methods for Analysis of Organic Compounds in Aqueous and Solid Samples", VTT Publications Technical Research Centre of Finland ESPOO, 2001, 71 pages.
Schwartz et al., "A Two-Dimensional Quadropole Ion Trap Mass Spectrometer", American Society for Mass Spectrometry vol. 13, 2002, United States, pp. 659-669.
Vestal, "Methods of Ion Generation", Chemical Reviews vol. 101, 2001, United States, pp. 361-375.
Wells et al., "A Quadrupole Ion Trap with Cylindrical Geometry Operated in the Mass-Selective Instability Mode", Analytical Chemistry vol. 70, No. 3, Feb. 1, 1998, United States, pp. 438-444.

* cited by examiner

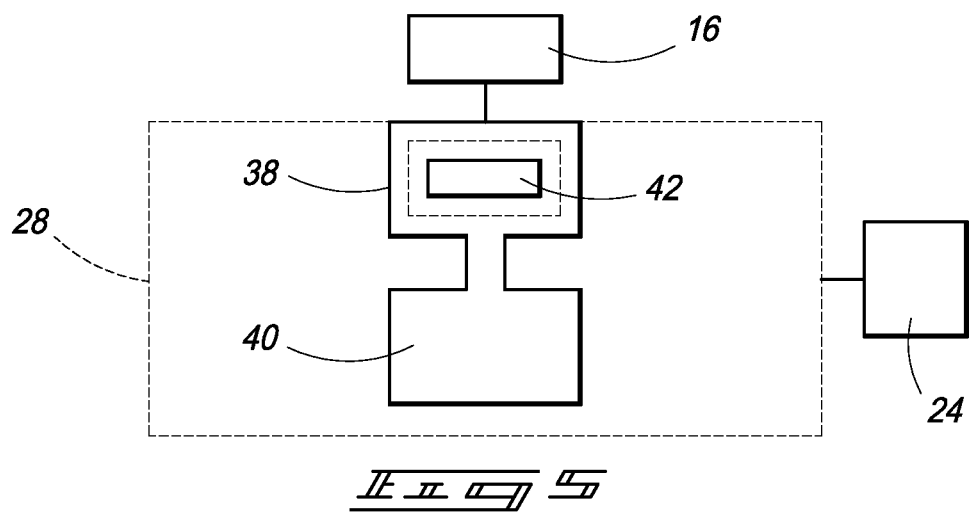
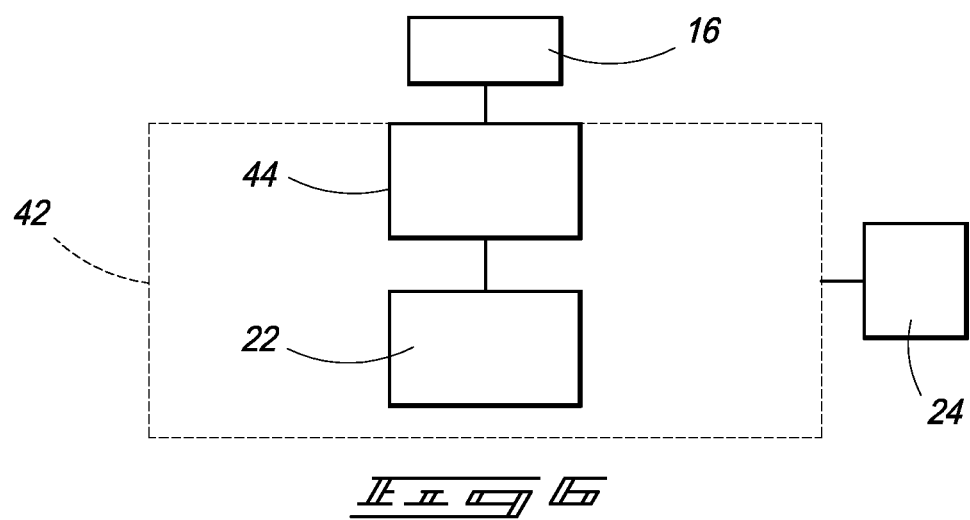

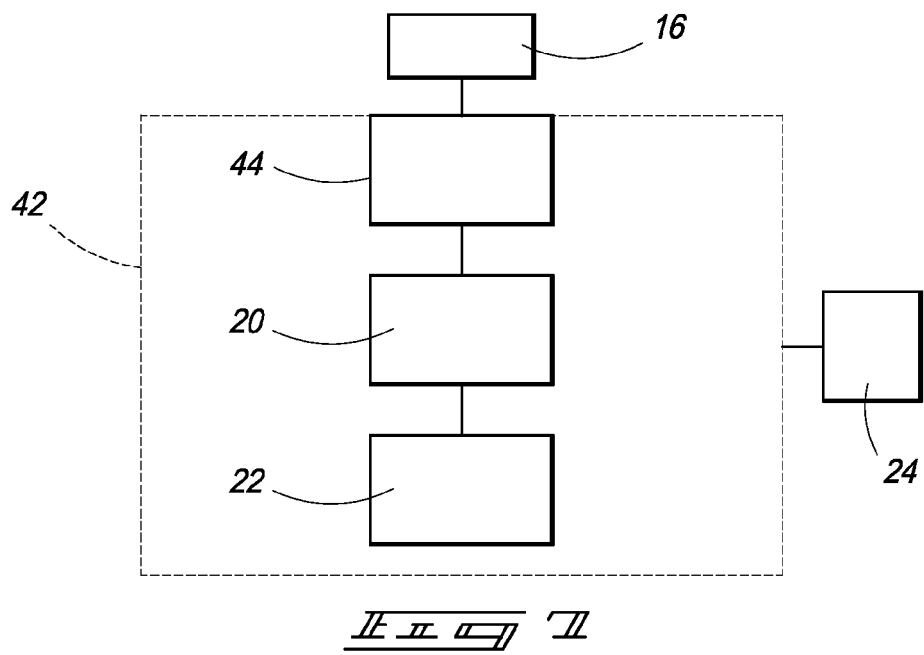
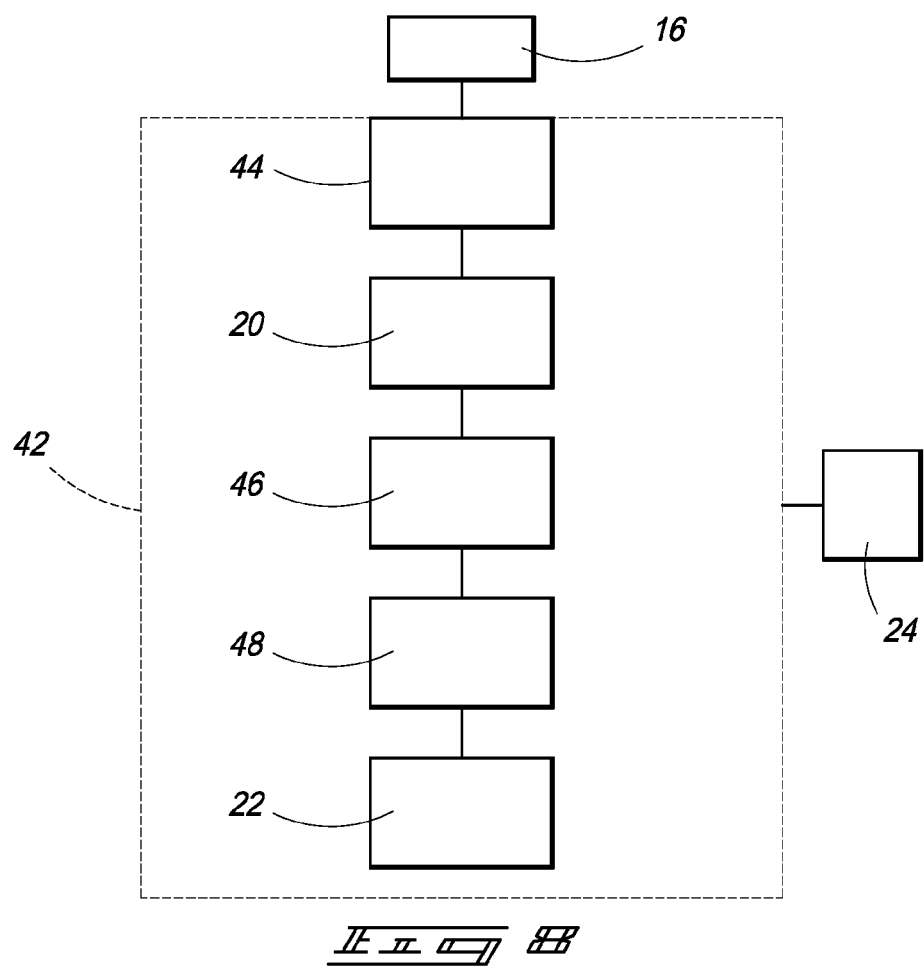

US 9,347,920 B2

ANALYTICAL INSTRUMENTS, ASSEMBLIES, AND METHODS

CROSS REFERENCE TO RELATED APPLICATION

This application is a continuation of U.S. patent application Ser. No. 12/981,024 filed Dec. 29, 2010, which is a continuation of U.S. patent application Ser. No. 11/629,953 filed Jul. 24, 2007, which is a 35 U.S.C. §371 of and claims priority to PCT International Application Number PCT/US2005/020783, which was filed 13 Jun. 2005 , and was published in English, which claims priority under 35 U.S.C. §119 to U.S. Provisional Patent Application No. 60/580,144 which was filed 15 Jun. 2004 and U.S. Provisional Patent Application No. 60/580,582 which was filed 16 Jun. 2004 , the entirety of each are incorporated herein by reference.

GOVERNMENT RIGHTS STATEMENT

This invention was made with Government support under SBIR Phase-I Contract M67854-04-C-3002 awarded by the United States Marine Corps. The Government has certain rights in the invention.

TECHNICAL FIELD

The present disclosure relates to analytical instruments, instrumentation, instrument assemblies, and analytical methods. More specific embodiments include mass analysis instrumentation as well as mass analysis methods.

BACKGROUND

Analytical instrumentation and particularly mass analysis instrumentation can be utilized to determine both the identity and amount of unknown compounds and mixtures. It is desirable to determine the identity and amount of unknown compounds and mixtures at their point of origin rather than obtaining a sample and transporting that sample to a laboratory for analysis, at least in that sampling and transportation of samples can contaminate the sample obtained and/or because sampling is not practical. Furthermore, it may be important to quickly ascertain the identity and amount of unknown compounds and sampling and transportation of the sample does not facilitate quick analysis.

Mass analysis instrumentation, such as mass spectrometers, are an exemplary analytical instrument recognized as being one of the most definitive detection techniques available. Mass spectrometers are capable of providing a reproducible signal that is diagnostic of almost any compound that can be introduced into the system. The capability that mass spectrometry provides is sought after for many uses including field applications where the instrument would ideally be brought to the sample rather than the more traditional transportation of the sample to the laboratory.

Typically analytical instrumentation of this sophistication is limited to laboratory use only and cannot be used in the field for practical reasons such as size or fragility. In the field, for example, instruments are not sheltered from inputs from the environment, the instruments can be exposed to travel which can jar and/or shock the instrument or other adverse conditions may occur. Accordingly, mass spectrometers may be limited to laboratory use for a variety of reasons, including the fragility of the mass spectrometer's vacuum system, which the instrument may be reliant upon to reduce the operating pressure within a mass spectrometer's mass analyzer. Depending on the type of mass analyzer used, higher pressure can cause a change in ion flight path, de-phasing of ion motion, etc., which can lead to the acquisition of erroneous data.

At least some analytical instrumentation and methods described herein provide an increased accommodation of environmental inputs such as shock which may be experienced in some analysis applications. Some embodiments of the analytical instrumentation and methods are portable and can be transported to where the chemistry happens, outside the laboratory.

SUMMARY OF THE DISCLOSURE

According to an embodiment, person-portable mass analysis instrumentation configured to perform multidimensional mass analysis are provided. Mass analysis instrumentation can include a mass analysis component coupled to a sample preparation component with a consumables-generation component coupled to the sample preparation component. The consumables-generation component can be configured to generate a composition used by the sample preparation component. The instrumentation can also include a housing coupled to one or more of the mass analysis component, the sample preparation component, and the consumables-generation component with the housing defining a space encompassing the instrument.

Mass analysis instrumentation are also provided that can include a housing encompassing components of the instrumentation, with the components including a processing and control component, a sample inlet component, a sample preparation component, a mass analysis component, and/or a detection component. The housing of the instrumentation can define a space having a volume of equal to or less than about 100,000 $cm^3$.

Instrument assemblies are provided that can include a housing coupled to an instrument component isolation assembly, wherein the component isolation assembly is isolated from an environment exterior to the housing. Exemplary instrument assemblies can include at least two instrument components configured to provide analysis, a first component and a second component. An instrument housing at least partially encompassing the first and second components can be provided, with the first component being rigidly affixed to the instrument housing. An instrument component isolation assembly can also be provided that is rigidly affixed to the second component with the isolation assembly being isolated from received inputs of the housing.

BRIEF DESCRIPTION OF THE DRAWINGS

Preferred embodiments of the invention are described below with reference to the following accompanying drawings.

FIG. 5 is an illustrative view of the instrument of FIG. 1 according to an embodiment.

FIG. 6 is an illustrative view of the instrument of FIG. 1 according to an embodiment.

FIG. 7 is an illustrative view of the instrument of FIG. 1 according to an embodiment.

FIG. 8 is an illustrative view of the instrument of FIG. 1 according to an embodiment.

DESCRIPTION

This disclosure is submitted in furtherance of the constitutional purposes of the U.S. Patent Laws "to promote the progress of science and useful arts" (Article 1, Section 8).

At least some embodiments provide analytical instruments, assemblies, and/or methods. Exemplary configurations of these instruments, assemblies, and/or methods are described with reference to FIGS. 1-19.

Figure 1:
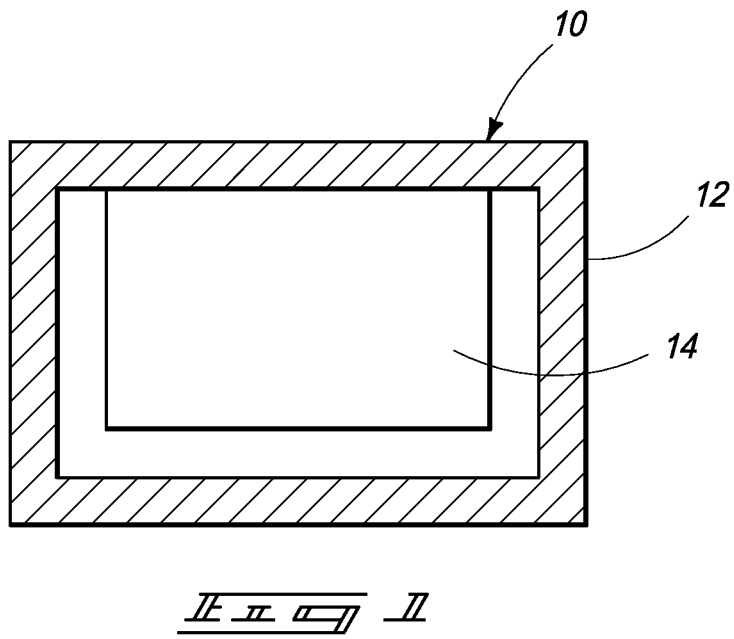
FIG. 1 is an illustrative view of an instrument according to an embodiment.

Referring first to FIG. 1, an exemplary analytical instrument 10 is depicted that includes a supporting structure 12 coupled to at least one of instrument components 14. Analytical instrument 10 can include mass analysis instrumentation such as mass spectrometry instrumentation, for example. The Minotaur 300 and 400 instruments available from Griffin Analytical Technologies, 3000 Kent Avenue, West Lafayette, Ind. 47906 are exemplary of instrument 10.

In exemplary embodiments, structure 12 can support, surround, and/or partially surround components 14. According to some embodiments, structure 12 can be referred to as a frame, base, case, cabinet, and/or any structure that can define a space occupied by components 14. An exemplary material of structure 12 includes aluminum. In some configurations the space defined by structure 12 is no greater than or equal to about 45.3×45.3×48.8 cm (100,142 $cm^3$) and in other exemplary embodiments the space defined by structure 12 is no greater than or equal to about 25.15×50.55×38.35 cm (48,756 $cm^3$). Components 14 can be configured to provide mass analysis including mass spectrometry analysis, for example. In exemplary configurations, instrument 10 can weigh less than 22.6 kgs.

Exemplary configurations of instrument 10 are person-portable. Person-portable instruments include those instruments that can be transported by an individual outside the traditional laboratory. These instruments can be self-contained including a power source, or they can be configured to be coupled to external power sources available in the field. Person-portable instruments are of a size and weight that allows them to be transported by a person of ordinary size and strength, including military personnel. Person-portable instruments can weigh less than 22.6 kgs and/or define a volume of less than or equal to about 100,000 $cm^3$ in some embodiments and in others the instrument can define a volume from about 100,000 $cm^3$ to about 50,000 $cm^3$. As discussed in more detail below, person-portable instruments can also be rugged in that they can be configured to withstand environmental inputs such as shock from physical impacts.

Figure 2:
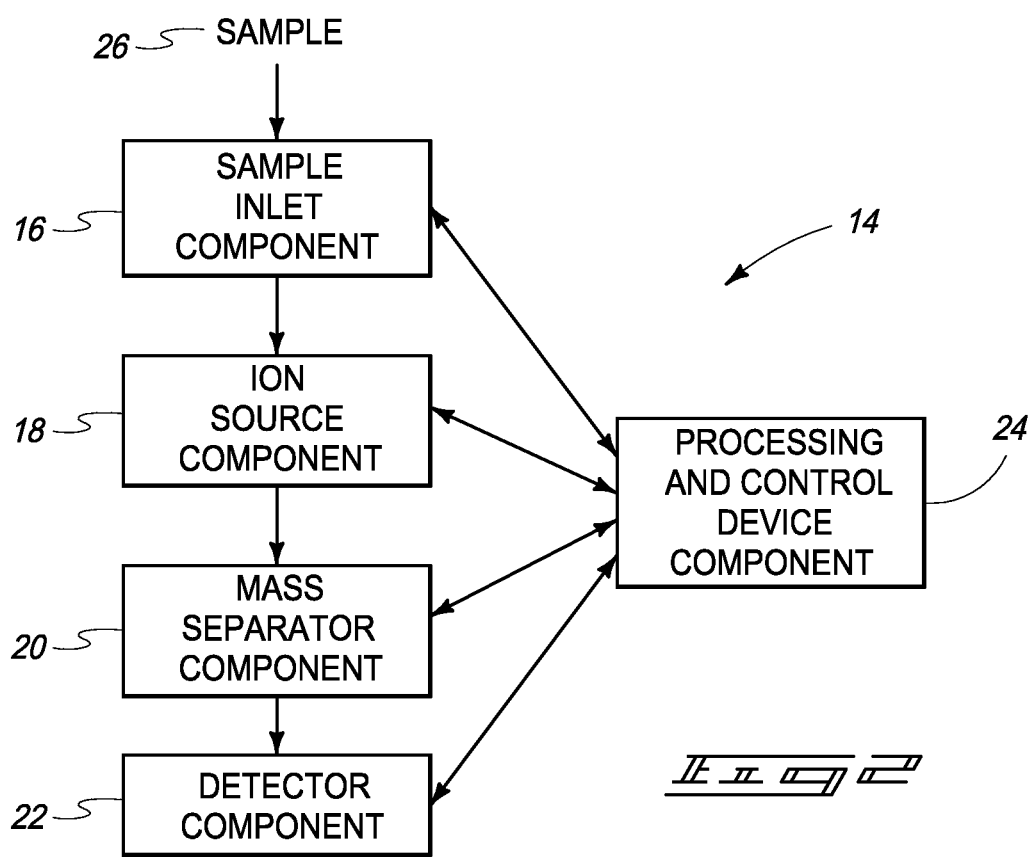
FIG. 2 is an illustrative representation of instrument components according to an embodiment.

With reference to FIG. 2, instrument components 14 can include mass analysis components, such as sample inlet component 16 operationally connected and/or coupled to an ion source component 18 which can be operationally connected and/or coupled to a mass separator component 20 which can be operationally connected and/or coupled to a detector component 22. Any and/or all of these components alone or in combination can be operationally connected and/or coupled to a processing and control device component 24. Exemplary embodiments provide for the use of components 14 to perform mass analysis including mass spectrometry. Components 14 can be operationally connected as shown in FIG. 2 or operationally connected in other configurations enabling mass analysis methods. Further, other arrangements including more or less or alternative components are possible.

As depicted in FIG. 2, a sample 26 can be introduced into sample inlet component 16. For purposes of this disclosure, sample 26 represents any chemical composition including both inorganic and organic substances in solid, liquid, and/or vapor form. Specific examples of sample 26 suitable for analysis include volatile compounds such as toluene or other specific examples including highly-complex non-volatile protein based structures such as bradykinin. In certain aspects, sample 26 can be a mixture containing more than one substance or in other aspects sample 26 can be a substantially pure substance. Analysis of sample 26 can be performed according to exemplary aspects described below.

Sample inlet component 16 can be configured to introduce an amount of sample 26 into instrument 10 (FIG. 1) for analysis. Depending upon sample 26, sample inlet component 16 may be configured to prepare sample 26 for ionization. Types of sample inlet components 16 can include batch inlets, direct probe inlets, chromatographic inlets, and permeable, semi-permeable, solid phase microextraction (SPME), and/or capillary membrane inlets. Exemplary inlets include those described in U.S. Provisional Patent Application Ser. No. 60/579,816 filed Jun. 14, 2004, entitled Sample Introduction Assemblies and Methods, the entirety of which is incorporated by reference herein. Sample inlet component 16 can also include means for preparing sample 26 for analysis in the gas, liquid, and/or solid phase. In some aspects, sample inlet component 16 may be combined with ion source component 18.

Ion source component 18 can be configured in exemplary embodiments to receive sample 26 directly or, in other exemplary embodiments, to receive sample 26 from sample inlet component 16. Ion source component 18 can be configured to convert portions or an entirety of sample 26 into analyte ions in one example. This conversion can include the bombardment of sample 26 with electrons, ions, molecules, and/or photons. This conversion can also be performed by thermal or electrical energy.

Ion source component 18 may utilize, for example, electron ionization (EI, typically suitable for the gas phase ionization), photo ionization (PI), chemical ionization, and/or electrospray ionization (ESI). For example, in PI, the photo energy can be varied to vary the internal energy of the sample. Also, when utilizing ESI, sample 26 can be energized under atmospheric pressure. Potentials applied when utilizing ESI can be varied to cause varying degrees of dissociation as described in International Application number PCT/US04/012849 filed Apr. 26, 2004, entitled Instrumentation, Articles of Manufacture, and Analysis Methods, the entirety of which is incorporated by reference herein. Furthermore, exemplary ion source components include those described in U.S. Provisional Patent Application No. 60/585,113 filed Jul. 2, 2004, entitled Spectrometry Instruments, Assemblies and Methods, the entirety of which is incorporated by reference herein.

Ion source component 18 can also be configured to fragment analytes without ionizing the analytes. In exemplary implementations, the analytes may be fragmented after ionization. An exemplary fragmentation technique includes collisionally activated disassociation.

The analyte ions can proceed from ion source component 18 to mass separator component 20, for example. Mass separator component 18 can include one or more of linear quadrupoles, triple quadrupoles, quadrupole ion traps (Paul), cylindrical ion traps, linear ion traps, rectilinear ion traps, ion cyclotron resonance, quadrupole ion trap/time-of-flight mass spectrometers, or other structures. Exemplary mass separator components include those described in International Patent Application No. PCT/US03/38587, filed Dec. 2, 2003, entitled Processes for Designing Mass Separators and Ion Traps, Methods for Producing Mass Separators and Ion Traps, Mass Spectrometers, Ion Traps, and Methods for Analyzing Samples, the entirety of which is incorporated by reference herein. Mass separator component 18 can also include focusing lenses as well as tandem mass separator components such as tandem ion traps or ion traps and quadrupoles in tandem. In one implementation, at least one of multiple tandem mass separator components can be an ion trap. Tandem mass separator components can be placed in series or parallel. In an exemplary implementation, tandem mass separator components can receive ions from the same ion source component. In an exemplary aspect, the tandem mass separator components may have the same or different geometric parameters. The tandem mass separator components may also receive analyte ions from the same or multiple ion source components.

Analytes may proceed to detector component 22 from mass separator component 20. Exemplary detector components include electron multipliers, Faraday cup collectors, photographic and scintillation-type detectors. Exemplary detector components also include those described in U.S. Provisional Patent Application No. 60/607,940 filed Sep. 7, 2004 entitled Mass Spectrometry Analysis Techniques and Mass Spectrometry Circuitry, the entirety of which is incorporated by reference herein.

Acquisition and generation of data can be facilitated with processing and control device component 24. Exemplary embodiments provide that the progression of mass spectrometry analysis from sample inlet component 16 to detector component 22 can be controlled and monitored by a processing and control device component 24. Processing and control device component 24 can be a computer or mini-computer or other appropriate circuitry that is capable of controlling components 14. This control can include, for example, the specific application of voltages to ion source component 18 and mass separator component 20, as well as the introduction of sample 26 via sample inlet component 16, and may further include determining, storing and ultimately displaying mass spectra recorded from detector component 22. Processing and control device component 24 can contain data acquisition and searching software. In one aspect, such data acquisition and searching software can be configured to perform data acquisition and searching that includes the programmed acquisition of total analyte count. In another aspect, data acquisition and searching parameters can include methods for correlating the amount of analytes generated to predetermine programs for acquiring data. Exemplary configurations of processing and control components include those described in U.S. Provisional Patent Application No. 60/607,890 filed Sep. 7, 2004, entitled Analysis Methods and Devices, as well as International Patent Application No. PCT/US04/29029 filed Sep. 4, 2003 entitled Analysis Device Operational Programming Methods and Analysis Device Methods, the entirety of both of which are incorporated by reference herein.

As the space defined by structure 12 (e.g., FIG. 1) can be considered small when compared to typical instruments, in exemplary embodiments, instrument 10 can be person-portable and/or packable and, components 14 can be configured to provide multiple levels of analysis (e.g., multidimensional analysis such as MS/MS) from a person-portable instrument. Structure 12 can be coupled to components 14 via attachment devices, and structure 12 may include openings (not shown) to allow access to components 14. These openings can remain open or structure 12 may include doors or panels allowing access to components 14 upon respective opening or removal.

Figure 3:
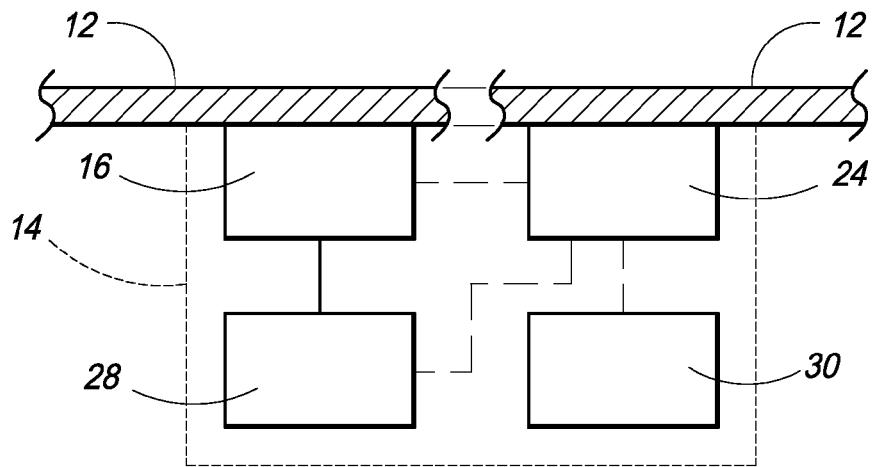
FIG. 3 is an illustrative view of the instrument of FIG. 1 according to an embodiment.

Referring to FIG. 3, an exemplary configuration of components 14 of instrument 10 are shown that can include at least one of sample inlet components 16 coupled to structure 12. Instrument components 14 can also include at least one of analysis components 28 coupled to at least one of sample inlet components 16 and at least one of processing and control components 24. Analysis components 28 can include components configured to perform analytical analysis including but not limited to components 18, 20, and 22 described above. As exemplarily depicted, at least one of processing and control components 24 can be coupled to at least one of sample inlet components 16 and structure 12. Embodiments of instrument components 14 include structure 12 only being coupled to at least one of sample inlet components 16 with none of processing and control components 24 being coupled to structure 12. Instrument components 14 can be configured to provide mass spectral data, for example. Instrument components 14 can further include power supply coupled to processing and control components 24 and, as necessary, inlet components 16 and analysis components 24. Exemplary power supply 30 can include portable batteries such as sealed lead-acid and/or lithium ion or polymer batteries. In other embodiments, power supply 30 may be located outside the space defined by structure 12.

Figure 4:
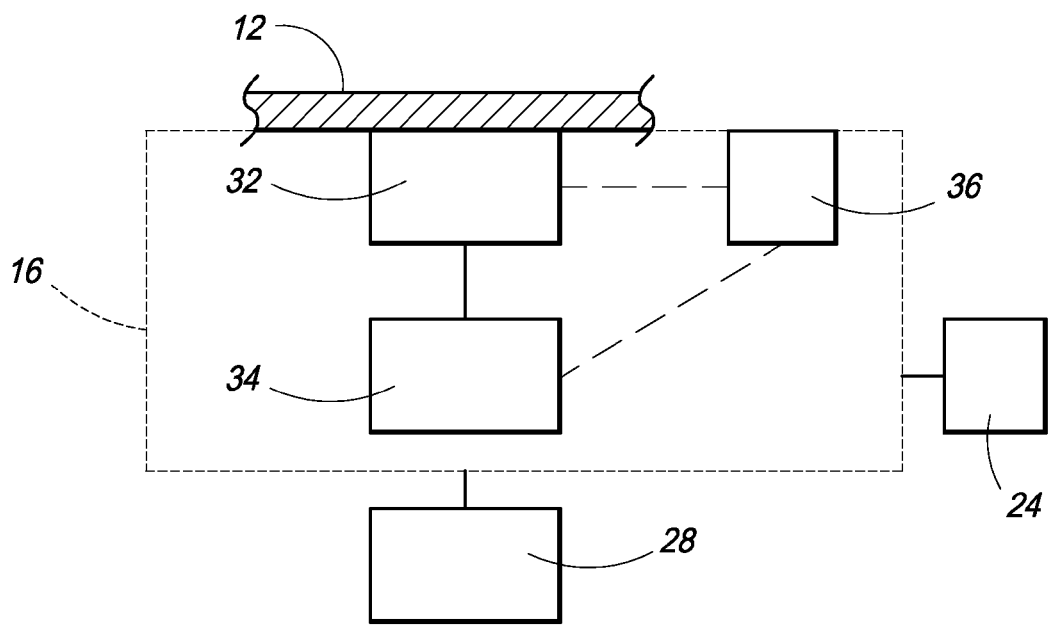
FIG. 4 is an illustrative view of the instrument of FIG. 1 according to an embodiment.

Referring to FIG. 4, sample inlet components 16 are shown that include sample introduction port 32 coupled to structure 12 and at least one of sample preparation components 34. Port 32 may be rigidly affixed to structure 12, for example. Sample introduction port 32 can be configured to receive a sample for analysis by instrument 10 (FIG. 1). Exemplary sample introduction ports 32 include syringe ports configured to receive the sample and convey the sample to sample preparation components 34.

Depending upon the sample, sample introduction port 32 may be configured to prepare the sample for introduction into sample preparation component 34 as well as remaining components 14 (FIG. 1). According to the exemplarily depicted embodiment of FIG. 4, sample introduction port 32 is configured to prepare the sample for introduction into sample preparation components 34. Sample introduction port 32 may be configured to convert the sample to a form suitable for transfer, for example, a solid sample can be converted to a liquid and/or a gas, or a liquid sample can be converted to a gas and/or a solid, likewise gases may be converted to liquids and/or solids depending on the configuration of instrument 10. Types of sample introduction ports 32 can include batch inlets, direct probe inlets, and permeable, semi-permeable, solid phase microextraction (SPME) and/or capillary membrane inlets. Sample inlet component 16 can be configured to utilized different sample introduction ports simultaneously. For example, sample introduction port 32 can be configured, in one embodiment, as parallel ports with one port configured to receive sample from a syringe and another port configured to receive sample from another instrument such as an automated air sampling device.

Sample preparation components 34 can be configured to prepare the sample received from port 32 for analysis by analysis components 28. As exemplarily depicted, sample preparation components 34 can be coupled to analysis components 28. According to alternative embodiments, analysis components 28 can be directly coupled to port 32. For example, analysis component 28 can be configured to receive the sample from the batch inlets, direct probe inlets, SPME, and/or capillary membrane inlets described above. In accordance with the exemplarily depicted embodiments of FIG. 4, sample preparation component 34 can be configured to separate the sample through, for example, chromatography. For example, component 34 can be configured as a gas chromatography apparatus. In exemplary embodiments, the gas chromatography apparatus can include capillary columns and in other embodiments the apparatus can be configured to perform fast gas chromatography.

As exemplarily depicted in FIG. 4, sample inlet component 16 can include consumables generator 36. In exemplary embodiments, consumables generator 36 can be configured to generate consumables for use during the operation of instrument 10. For example, where sample preparation component 34 is configured to process the sample by gas chromatography, consumables generator 36 can be configured to provide carrier gas to the gas chromatograph. In exemplary embodiments, generator 36 is configured as a nitrogen generator and nitrogen is utilized as a carrier gas during the gas chromatography performed by sample preparation component 34. Generator 36 can also include a helium generator, and/or in exemplary embodiments, generator 36 can include an air purifier. Nitrogen, helium, and air exemplary of compositions that may be combined with samples to facilitate analysis, such as carrier gases. Generator 36 can also include a tank and/or reservoir of the composition, such as nitrogen, helium, and/or air. Exemplary aspects also include generator 36 configured to provide consumables to port 32. For example, in the case where port 32 is configured to be flushed either before or after the sample is received, generator 36 can be configured to provide flushing gases to port 32. In exemplary embodiments, high vacuum pumps such as turbo pumps can be configured at the diaphragm head of a rough pump. In exemplary embodiments, generator 36 can be used external to instrument 10. Exemplary aspects also include providing consumables from outside instrument 10, such as configuring instrument 10 to be coupled to a tank of consumable carrier gas.

Referring to FIG. 5, analysis components 28 are depicted that include analysis chamber 38 coupled to vacuum component 40. Analysis chamber 38 can be coupled to sample inlet components 16 to facilitate the progression of sample from sample introduction port 32 (FIG. 4). Analysis chamber 38 is typically maintained under sufficient vacuum to facilitate mass spectrometry analysis. Analysis chamber 38 can be constructed of aluminum or stainless steel, but other materials sufficient to maintain vacuum will be appropriate. Vacuum component 40 is configured to provide sufficient vacuum within analysis chamber 38 to facilitate mass spectrometry analysis. Exemplary vacuum components 40 include getter pumps, piston pumps, and/or turbo pumps. In exemplary embodiments, rugged pumps capable of providing sufficient vacuum can be utilized. In exemplary embodiments, vacuum component 40 can include both a high vacuum pump and a rough pump. In exemplary implementations, the rough pump and high vacuum pump can be configured to share common components such as circuitry and/or power supply. Components 28 include those described in International Patent Application No. PCT/US04/01144, filed Jan. 16, 2004, entitled Mass Spectrometer Assemblies, Mass Spectrometry Vacuum Chamber Lid Assemblies, and Mass Spectrometer Operational Methods, the entirety of which is incorporated by reference herein.

At least portions of mass analysis components 42 can be within analysis chamber 38. In exemplary embodiments, analysis components 42 can be configured to be modular, thereby facilitating sufficient maintenance and/or removal and replacement. Mass analysis components 42 can include one or more of components 18, 20, and/or 22 described herein. An exemplary chamber 38, including components 42 is described in International Patent Application No. PCT/US04/01144 filed Jan. 16, 2004, entitled Mass Spectrometer Assemblies, Mass Spectrometry Vacuum Chamber Lid Assemblies, and Mass Spectrometer Operational Methods, the entirety of which is incorporated by reference herein.

Referring to FIG. 6, an exemplary configuration of analysis components 42 is depicted that includes an analyte modification component 44 coupled to both sample inlet component 16 and detector component 22. Analyte modification component 44 can be configured, in exemplary embodiments, to receive the sample directly from port 32 (FIG. 4) or, in other exemplary embodiments, to receive the sample from sample preparation component 34 (FIG. 4). Analyte modification component 44 can be any component configured to modify an analyte upon exposure of the analyte to the analyte modification component. For example, analyte modification component 44 can be configured as an ionization component to process/ionize the sample according to one or more parameters to form ionized analytes, such as component 18 described above. In this configuration, analyte modification component parameters include ionization parameters that can include parameters that affect one or more of the amount of ionization, dissociation, and/or fragmentation of the sample when exposed to analyte modification component 44. The formation of ionized analytes from the sample can include the bombardment of the sample with electrons, ions, molecules and/or photons. The formation of ionized analytes within analyte modification component 44 can also be performed by thermal or electrical energy according to the ionization parameter and its value.

Analyte modification component 44 may be configured as, for example, an electron ionization component (EI, typically suitable for gas phase ionization), a photo ionization component (PI), a chemical ionization component, collisionally activated dissociation component (CID), electrospray ionization (ESI), Flame Ionization, and/or Atmospheric Pressure Chemical Ionization (APCI). Analyte modification component 44 can be configured to operate with other components. In exemplary embodiments, both an EI and CID may be configured in line or parallel to receive and modify sample.

In reaction form, an exemplary analyte modification is demonstrated by equation 1 below:

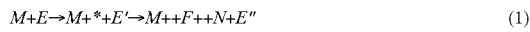  (1)

wherein M represents the neutral analyte, E represents the energy provided to M; M+* represents an internally excited ion; E' represents any E not deposited into M+* as internal or kinetic energy; M+, F+ and N represent charged analyte, charged dissociation products, and neutral dissociation products, respectively; and E'' represents any E not remaining in M+, F+ or N as internal or kinetic energy. In one embodiment, analyte modification component 44 can impact the amount of dissociation of sample into these other molecules (F+ and N).

Analyte modification component 44 can also include analyte derivitisation components such as chemical derivitisation components for use in combination with gas chromatography and or liquid chromatography sample preparation components. Furthermore, embodiments are contemplated that include analyte modification component 44 configured as multiple components, such as both an electron impact ionization source and a chemical ionization source.

Other contemplated embodiments include acquiring a data set with analyte modification component 44 configured in one configuration and acquiring another data set with analyte modification component 44 in another configuration. For example, a data set can be acquired with analyte modification component 44 configured as an electron ionization component and another data set can be acquired with analyte modification component 44 configured as a chemical ionization component.

Samples modified in analyte modification component 44 can be detected in detection component 22, for example. Exemplary detection components include electron multipliers, Faraday cup collectors, photographic, and scintillation-type detectors as described above.

Referring next to FIG. 7, components 42 are shown that include mass separator component 20 coupled to analyte modification component 44 and detector component 22. Processing and control components 24 can be coupled to components 42 as well as modification, mass separator, and/or detector components 44, 20, and/or 22 respectively. Mass separator component 20 can include one or more of linear quadrupoles, triple quadrupoles, quadrupole ion traps (Paul), cylindrical ion traps, linear ion traps, rectal linear ion traps, ion cyclotron resonance, time-of-flight mass spectrometers, ion mobility or other structures. Mass separator component 20 can also include focusing lenses as well as tandem mass separator components such as tandem ion traps or an ion trap and quadrupole ion trap in tandem.

In one implementation, at least one of the multiple tandem mass separator components can be an ion trap. Tandem mass separator components can be placed in series or parallel. In an exemplary implementation, tandem mass separator components can receive ions from the same analyte modification component 34. In an exemplary aspect, the tandem mass separator components may have the same or different geometric parameters. The tandem mass separator components may also receive analyte ions from the same or multiple analyte modification components 44. In exemplary implementations, mass separator component 20 can be configured to provide multidimensional mass separation and/or analysis. When configured for multidimensional mass analysis, the instrument can provide for the analysis of mixtures without the aid of the sample preparation component as described above, gas and/or liquid chromatography, for example.

An exemplary mass separator component 20 useful in accordance with one embodiment is a cylindrical ion trap (CIT). CITs typically include three components: a trapping volume; and two endcaps. Typically an AC current or RF voltage is applied to the trapping volume at a predefined rate (e.g., controlled by 50) to eject trapped analytes which are subsequently detected. RF voltage ramps may include variables such as power and/or frequency. Combinations of these variables in predefined amounts are typically referred to as waveforms. Generally, waveforms can be optimized to increase detection of specific analytes of interest. Waveforms can also be optimized to allow for multiple stages of mass analysis.

In an exemplary embodiment, mass separator component 20 can be a cylindrical ion trap and the mass separator parameter of the cylindrical ion trap can be a parameter that influences the mass-to-charge ratio of ionized analytes received by detector component 22. An exemplary cylindrical ion trap parameter value that influences the mass-to-charge ratio of ionized analytes received by detector component 22 is a mass-to-charge ratio range that can be specified as waveform values.

Referring to FIG. 8, spectrometry components 42 are shown configured having analyte modification component 46 coupled to mass separator component 48 in addition to previously detailed components 44, 20, and 22, for example. The configuration of spectrometry component 42 in FIG. 8 is sometimes referred to as a MS/MS or a tandem mass separator configuration.

As exemplarily depicted, analyte modification component 44 can be configured to receive the sample from sample inlet component 16 and provide, in one embodiment, an ionization energy to the sample to form a group of ionized analytes. In an exemplary aspect, analyte modification component 44 can be configured to provide ionization energy to the sample to form a first group of ionized analytes. Mass separator component 20 can be configured to receive the first group of ionized analytes and provide a first separation waveform to separate a first mass-to-charge ratio range of the first group of ionized analytes. Analyte modification component 46 can be configured to receive the first range of ionized analytes and provide a second analyte modification component parameter value to the first range of ionized analytes to form a second group of ionized analytes. Mass separator component 48 can be configured to receive the second group of ionized analytes and provide a second separation waveform to separate a second mass-to-charge ratio range of the second group of ionized analytes. Detector component 22 can be configured to detect the ionized analytes of the ranges received from mass separator component 48.

Figure 9:
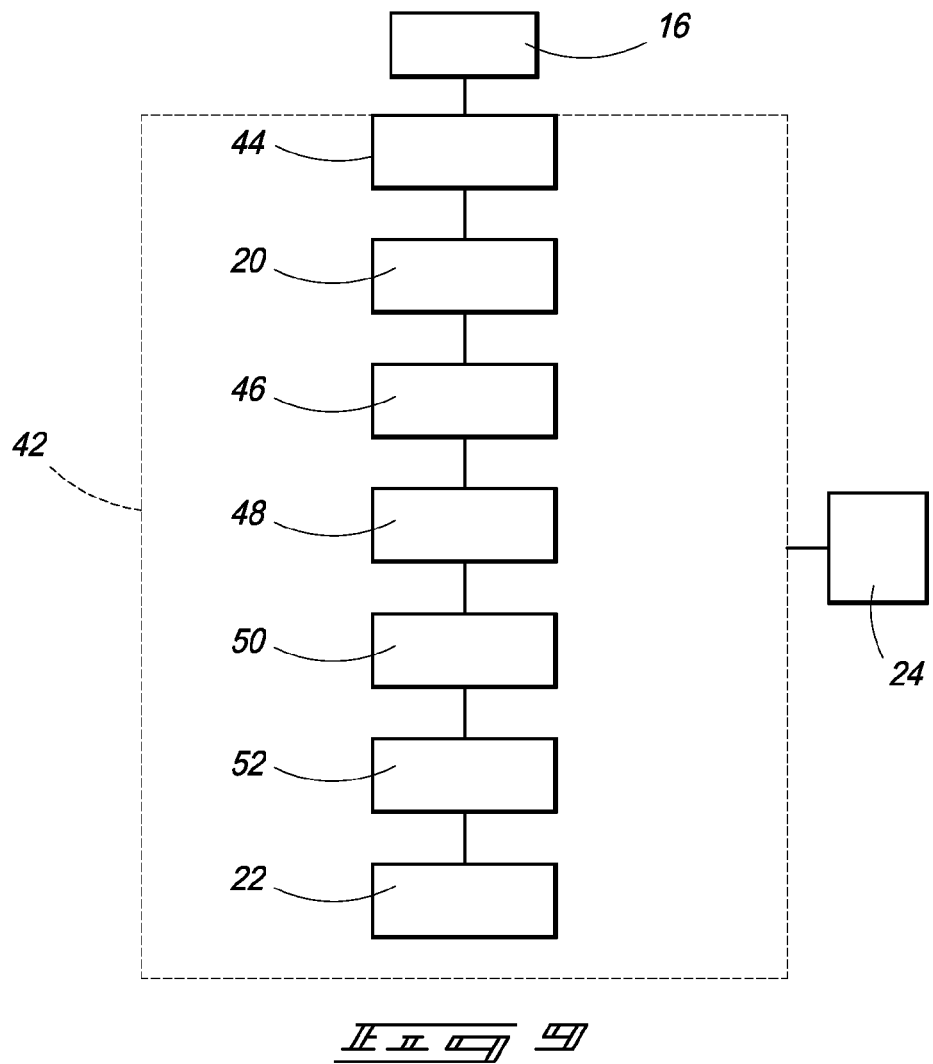
FIG. 9 is an illustrative view of the instrument of FIG. 1 according to an embodiment.

Referring next to FIG. 9, spectrometry components 42 can be configured, as shown, to include analyte modification component 50 coupled to mass separator component 52 in addition to components 44, 20, 46, 48, and 22 already detailed above. In an exemplary embodiment, spectrometry components 42 are configured to perform MS/MS/MS. As configured in FIG. 8, spectrometry components 42 can add an additional level of spectrometry to spectrometry component 42 as configured in FIG. 7. All the components described above can be controlled, monitored, and/or have data acquired from by processing and control components 24. In exemplary embodiments, all, or at least more than one of, the components described above can be coupled to processing and control components 24.

Figure 10:
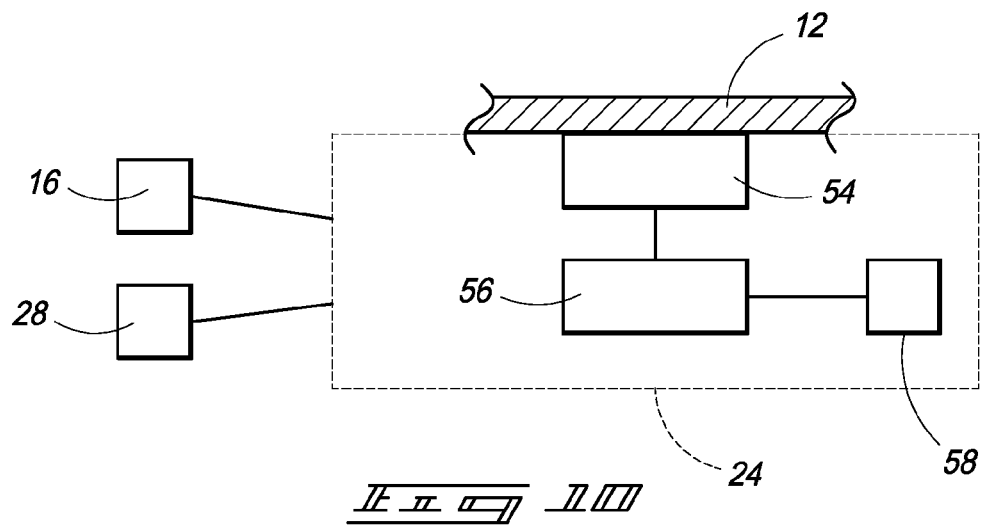
FIG. 10 is an illustrative view of the instrument of FIG. 1 according to an embodiment.

Referring to FIG. 10, processing and control component 24 is shown having user interface 54 coupled to structure 12 of instrument 10 (FIG. 1). Processing and control component 24 can also include processing circuitry 56 coupled to both user interface 54 and storage circuitry 58.

According to one embodiment, user interface 54 can be coupled to structure 12 and provide user access to process circuitry 56. User interface 54 can take the form of a touch screen aligned with the exterior of structure 12 in exemplary embodiments, and user interface 54 can be within the volume defined by structure 12 and access to user interface 54 can be had through access panels, doors or openings in structure 12. In other embodiments, user interface 54 can be a computer interface that is configured to provide access to another process and control component, for example a stand alone computer. In exemplary embodiments, the computer interface can be a wireless interface and in other embodiments, the computer interface can take the form of a TCP/IP or a standard LAN connection. In exemplary embodiments, instrument 10 can be configured to accumulate and store sample data unattended. In other embodiments, instrument 10 can be configured to allow access to data and further provide for the manipulation of the data acquired. According to another embodiment, instrument 10 can be configured to send data to a remote computer upon acquisition.

In one embodiment, the progression of analysis from sample inlet component 16 to analysis component 28 can be controlled and/or monitored by processing circuitry 56 in the described exemplary embodiment. Processing circuitry 56 may be implemented as a processor or other structure configured to execute executable instructions including, for example, software and/or firmware instructions. Other exemplary embodiments of processing circuitry 56 include hardware logic, PGA, FPGA, ASIC, and/or other structures. These examples of processing circuitry 56 are for illustration and other configurations are possible.

Processing circuitry 56 can be configured to control the values of analytical component parameters defined by the user of instrument 10 and/or monitor the components described above. Control of the analytical component parameter values by processing circuitry 56 can include, for example, dictating a predefined application of ionization energy by modification components 44, 46, and/or 50, for example. Exemplary monitoring includes the recording of data received from detector component 22. By varying analytical component parameter values, sample characteristics and/or data can be obtained. Exemplary sample characteristics and data can include mass spectra.

In one aspect, processing circuitry 56 may execute data acquisition and searching programming and be configured to perform data acquisition and searching that includes the acquisition of sample characteristics such as total ion current or mass spectra. In another aspect, processing circuitry 56 can be configured to associate detected sample characteristics such as total ion current responsive to one or more analytical parameters such as an ionization parameter including electron impact ion source energy.

Processing circuitry 56 can be configured to store and access data from storage circuitry 58. Storage circuitry 58 is configured to store electronic data and/or programming such as executable instructions (e.g., software and/or firmware), data, or other digital information, and may include processor-usable media. Processor-usable media includes any article of manufacture which can contain, store or maintain programming, data and/or digital information for use by or in connection with an instruction execution system including processing circuitry, in the exemplary embodiment. For example, exemplary processor-usable media may include any one of physical media such as electronic, magnetic, optical, electromagnetic, and infrared or semiconductor media. Some more specific examples of processor-usable media include, but are not limited to, a portable magnetic computer diskette, such as a floppy diskette, zip disk, hard drive, random access memory, read only memory, flash memory, cache memory, and/or other configurations capable of storing programming, data, or other digital information. Embodiments also include configurations where processing and control components 24 can be configured to acquire sample data and analyze acquired data unattended. For example, sample inlet component 16 can be configured as an auto-sampler and, in exemplary embodiments, air samples can be acquired at predefined intervals as dictated by processing and control component 24. Processing and control component 24 can be configured according to predefined user parameters to acquire sample data. In other embodiments, processing and control component 24 can be configured to forward data and/or instrument status to remote locations via wireless and/or wired communication.

Figure 11:
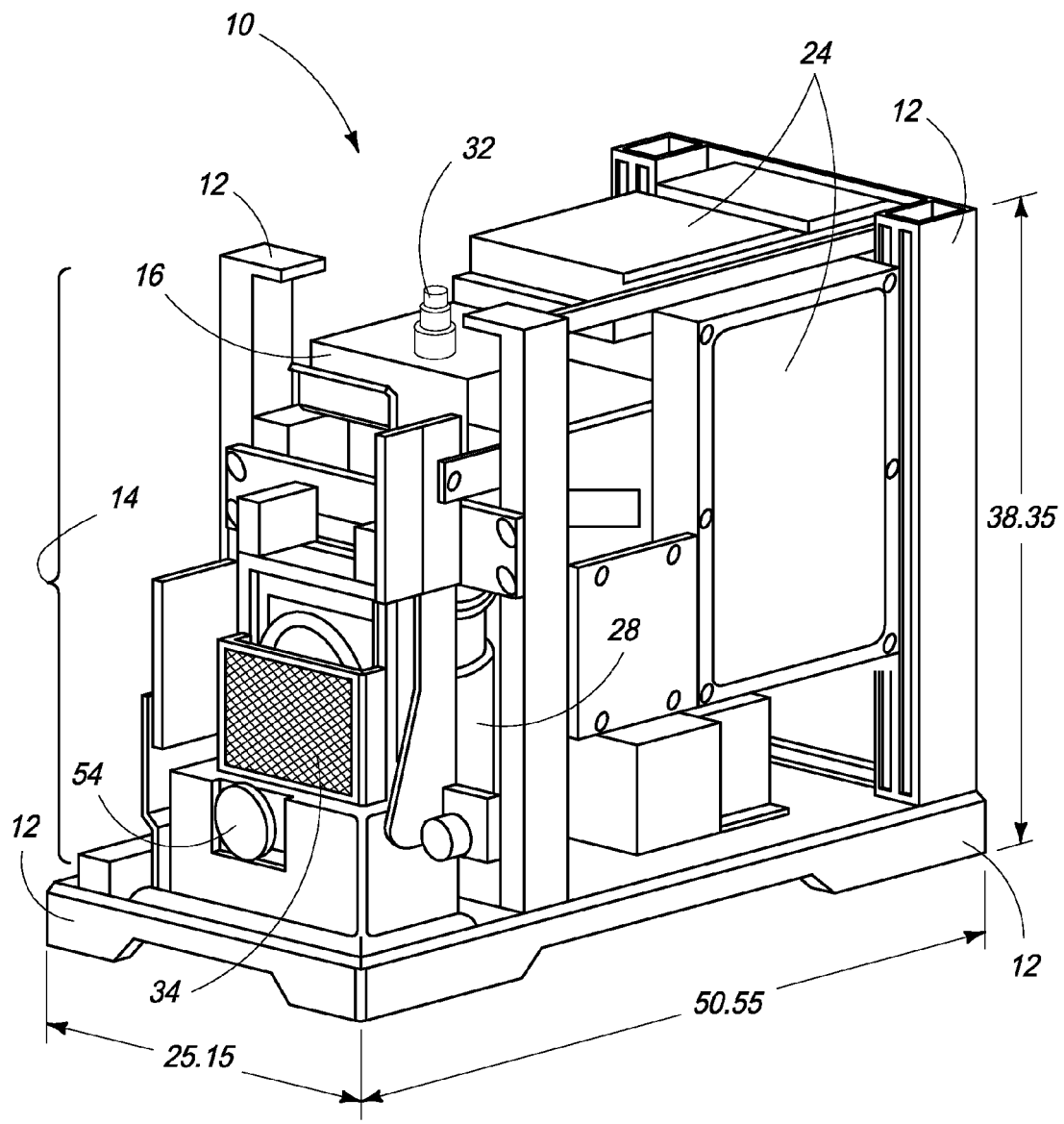
FIG. 11 is an isometric view of the instrument of FIG. 1 according to an embodiment.

Referring next to FIG. 11, mass spectrometry instrument 10 can be configured as shown that includes structure 12 defining a volume within which components 14 reside. As exemplarily depicted, components 14 include sample introduction port 32 above analysis component 28 with sample preparation component 34, in this case, a gas chromatography column, placed adjacent analysis component 28. Analysis components 28 are configured to perform multidimensional analysis, such as the MS/MS analysis as described above. Instrument 10 of FIG. 11 can also include processing and control components 24 proximate the exterior of instrument 10. In particular embodiments, components 24 can be integrated into access panels (not shown) or doors (not shown) of structure 12. As exemplarily depicted, instrument 10 is configured to have user interface 54 located at the lower front portion of structure 12. As depicted, interface 54 includes at least one gauge and valves to control sample inlet components 32 and 34. As illustrated, instrument 10 has a width of 25.15 cm, a depth of 50.55 cm, and a height of 38.35 cm. As exemplarily depicted in FIG. 11, structure 12 can define a space encompassing instrument components 14 of less than or equal to about 50,000 $cm^3$.

Figure 12A:
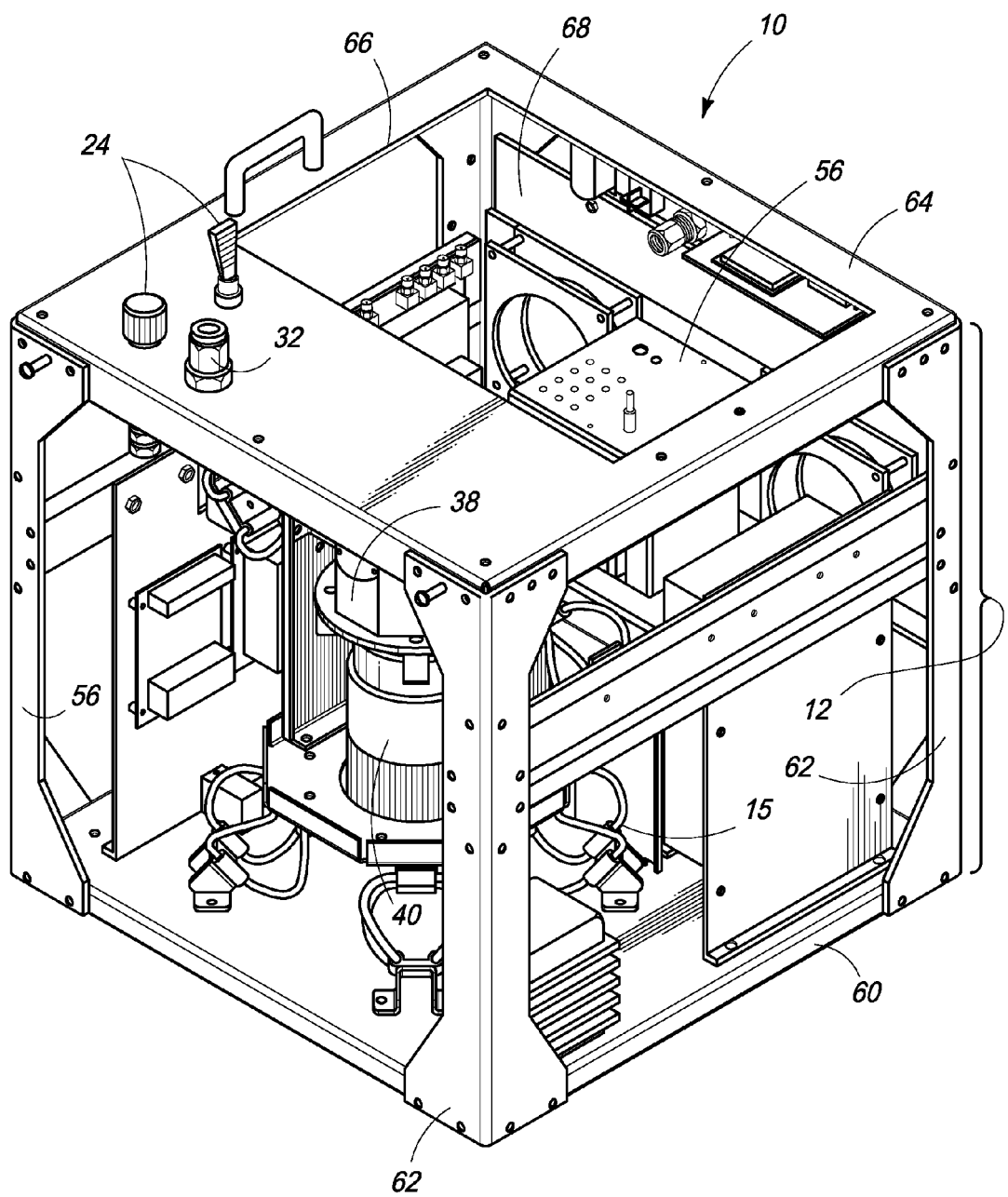
FIG. 12A is an isometric view of the instrument of FIG. 1 according to an embodiment.

Referring to FIGS. 12A-E, instrument 10 may be configured as shown to include housing 12 according to an exemplary embodiment. As depicted in FIG. 12A, housing 12 is configured as a frame having a base or floor 60 with supports or sidewalls 62 extending vertically therefrom and supporting a top 64. Top 64 can be configured with access opening 66. Access opening 66 can be configured to provide access to instrument components within the space defined by housing 12, as described above. For example, access opening 66 can provide access to processing circuitry 56. Top 64 can also be coupled to processing and control components 24 and sample introduction port 32. As exemplarily depicted, analysis chamber 38 and vacuum component 40 are encompassed by housing 12. Instrument 10 of FIG. 12A can be configured with openings 68 fabricated into housing 12, for example. Openings 68, in exemplary embodiments, can be configured to receive motorized fans that in some embodiments can facilitate cooling of the space defined by housing 12.

Figure 12B:
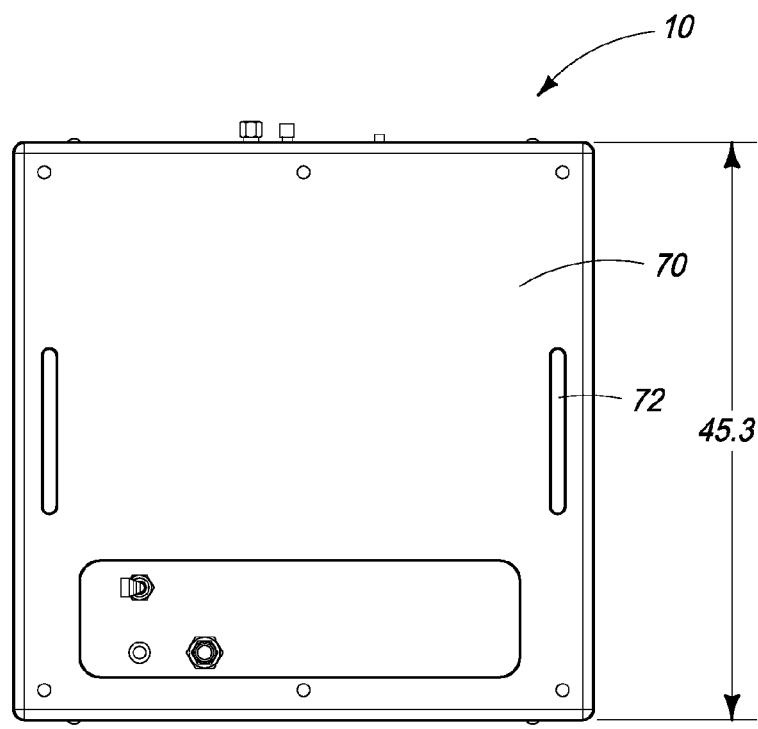
FIG. 12B is top view of the instrument of FIG. 12A according to an embodiment.
Figure 12C:
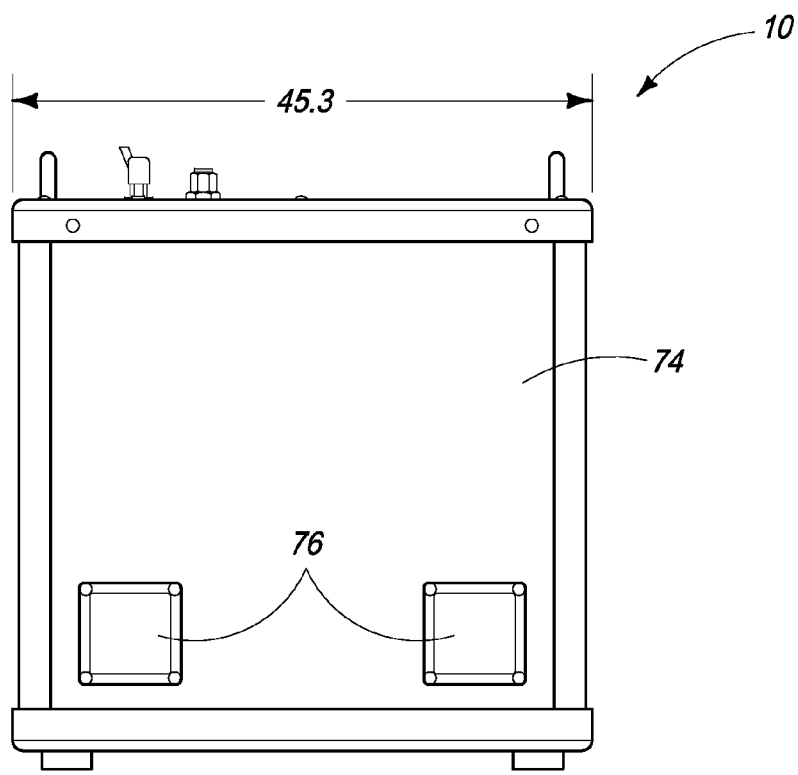
FIG. 12C is a front view of the instrument of FIG. 12A according to an embodiment.
Figure 12D:
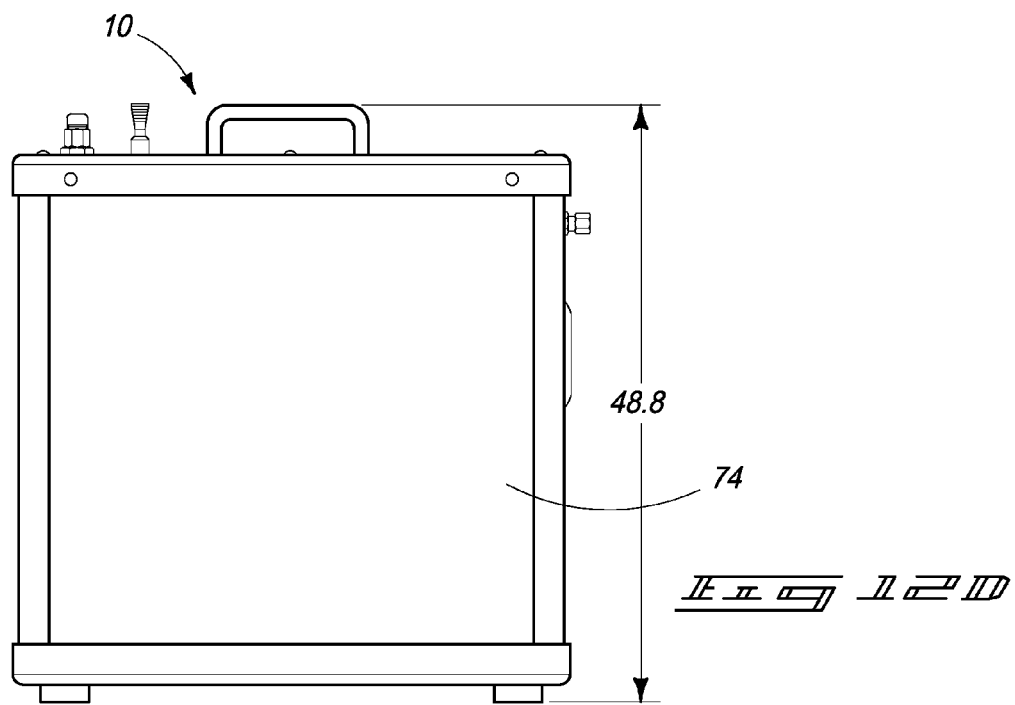
FIG. 12D is a side view of the instrument of FIG. 12A according to an embodiment.
Figure 12E:
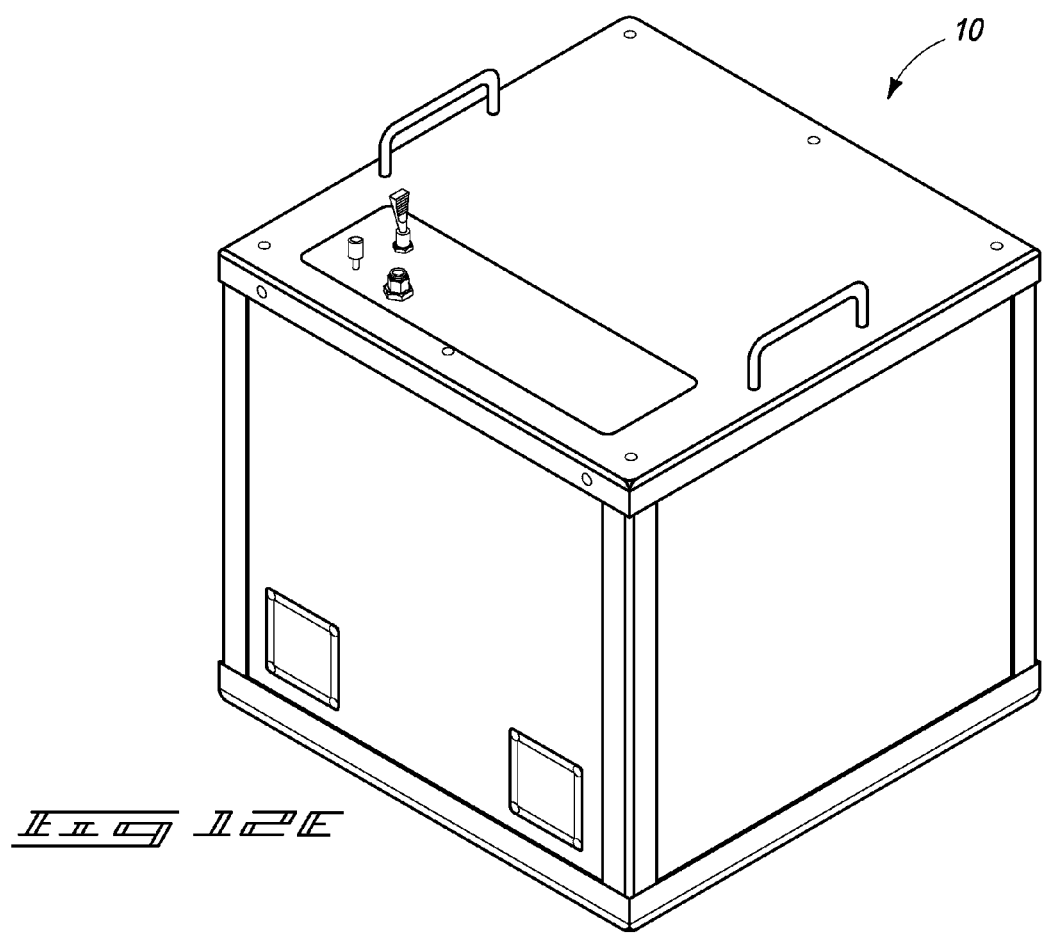
FIG. 12E is an isometric view of the instrument of FIG. 12A according to an embodiment.

Referring to FIG. 12B, a top view of instrument 10 of FIGS. 12A-E is shown with instrument 10 configured with a cover 70 over top 64. Cover 70 can include handles 72 that can facilitate the portability of instrument 10, for example. As illustrated, the depth of instrument 10 can be 45.3 cm. Referring to FIG. 10C, a front view of instrument 10 of FIGS. 12A-E is shown with side panel 74 in place over the frame and access panels 76 in place in side panels. As illustrated, the width of instrument 10 of FIG. 12A-E can be 45.3 cm. According to exemplary embodiments, panels 76 can be removed and/or replaced with vent covers. In an exemplary aspect, when panels 76 are removed or replaced with vent covers cooling of the spaced defined by housing 12 can be facilitated by directing air intake from these vent covers through the space to fans in openings 68 (FIG. 12A) for example. Referring to FIG. 12D, a side view of instrument 10 of FIGS. 12A-E is shown with side panel 74 in place over the frame. As illustrated, the height of instrument 10 can be 48.8 cm. FIG. 12E is exemplary of a perspective view of instrument 10 as exemplarily depicted in FIGS. 12A-E.

At least some of the embodiments of the description provide instrumentation and assemblies as well as instrumentation isolation components and systems including instrumentation operational methods. Exemplary configurations of these assemblies and methods are described with reference to FIGS. 13-19.

Figure 13:
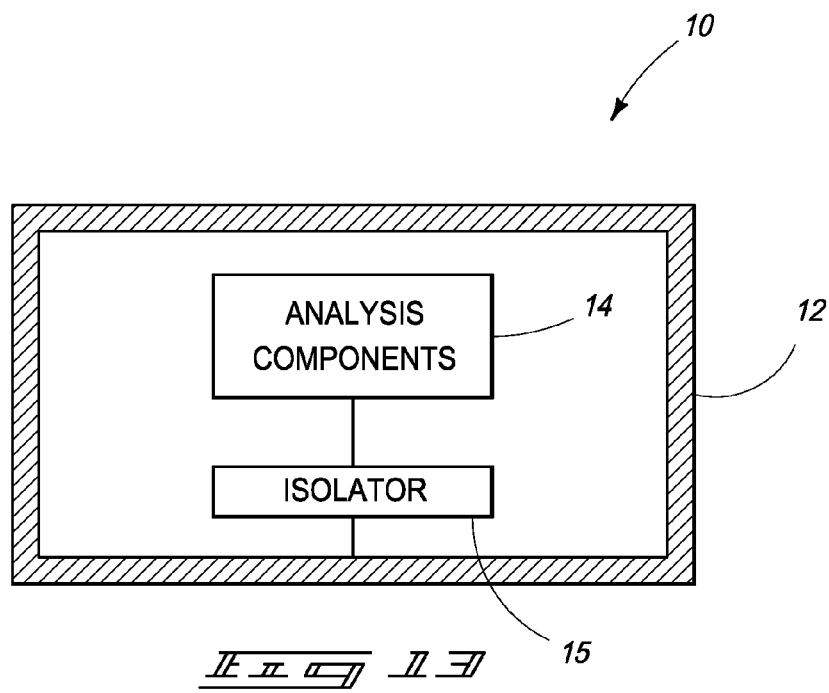
FIG. 13 is an illustrative representation of an instrument assembly according to an embodiment.

Referring first to FIG. 13, an exemplary embodiment of instrument 10 is shown that includes housing 12 at least partially encompassing analysis components 14. In the shown embodiment, components 14 are isolated from housing 12 by an isolator 15. In the shown embodiment, housing 12 at least partially encompasses isolator 15. Isolator 15 isolates components 14 from at least some inputs experienced by housing 12, in one embodiment. Inputs experienced by housing 12 can include inputs from the surrounding environment of instrument 10. Exemplary inputs include those of shock, vibration, electrical, and/or thermal inputs. An exemplary isolator 15 includes a shock-mount system. Such an isolator 15 can include a plurality of shock-mounts or a singular shock-mount. Exemplary isolators can include wire rope isolators. While depicted in FIG. 13 as a single isolator, isolator 15 can include a plurality of isolators and, in other embodiments these isolators can be placed at desired locations isolating components 14 from housing 12. In exemplary embodiments, the entirety of instrument 10 may be isolated by isolating the instrument from its environment through the use of isolators between it and, in exemplary implementations, a base, platform, and/or floor, while at the same time isolating all or a portion of components 14 from housing 12.

Exemplary components 14 include those described above (FIG. 2), such as components 18, 20, and/or 22, in analysis chamber 38 being coupled to a vacuum component 40. To achieve the vacuum within the analysis chamber single or multiple pumps can be utilized as vacuum component 40. Exemplary pumps include those that do not require any moving parts, such as ion pumps and getter pumps. Components 14 can be configured as the mass spectrometer described in U.S. Pat. No. 5,426,300, herein incorporated by reference. According to some embodiments, ion and getter type pumps cannot provide significant levels of pumping capacity for extended periods of time especially when a high flow of carrier gas into the apparatus is utilized. This can be the case when gas chromatography is utilized as a sample introduction component, as a carrier gas is utilized to transport the sample through the sample inlet and thus requires some flow of gas into the mass spectrometer's vacuum chamber. An exemplary pump having moving parts that may be utilized is a turbomolecular pump, which can be fragile.

Figure 14:
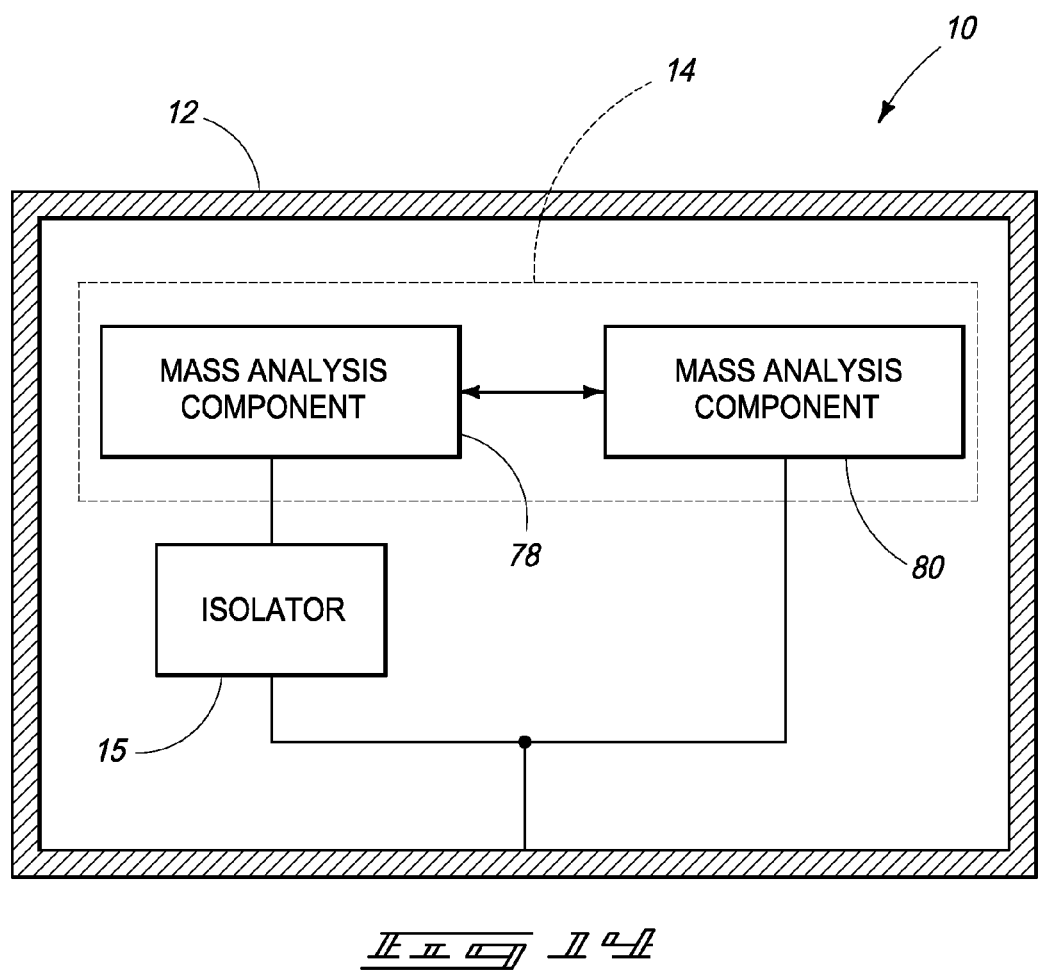
FIG. 14 is an illustrative representation of the instrument assembly of FIG. 13 according to an embodiment.

Referring next to FIG. 14, an exemplary embodiment of instrument 10 is shown that includes a housing 12 at least partially encompassing components 14. As exemplarily depicted in FIG. 14, components 14 include mass analysis components 78 and 80 which may correspond to one or more of components 28 described above. As depicted in FIG. 14, component 78 can be isolated from received inputs (e.g., experienced by housing 12) by isolator 15 while at the same time component 80 is rigidly affixed to housing 12. In other arrangements all components of the instrument may be isolated using one or more of isolator 15. Isolator 15 can include shock-mounts. Shock-mounts can be chosen based on the highest shock anticipated, the level of shock that can be transferred to the instrument after shock distribution, the weight of the instrument, and/or the amount of travel space available within the space defined by housing 12. Component 78 that is isolated from housing 12 by isolator 15 can include vacuum component 40, such as the turbomolecular pump. Component 78 can also include fragile components of analysis components 14. Component 80 can include those components more rugged and able to be affixed to housing 12 that are not as susceptible to shock and/or environmental inputs received by housing 12. Isolator 15 can also include a shock-mount and/or component isolation assembly. Component 18 can be flexibly coupled to component 78, for example, via flexible tubing and/or configuring the components within instrument 10 to allow for sufficient space for motion between the components.

Figure 15:
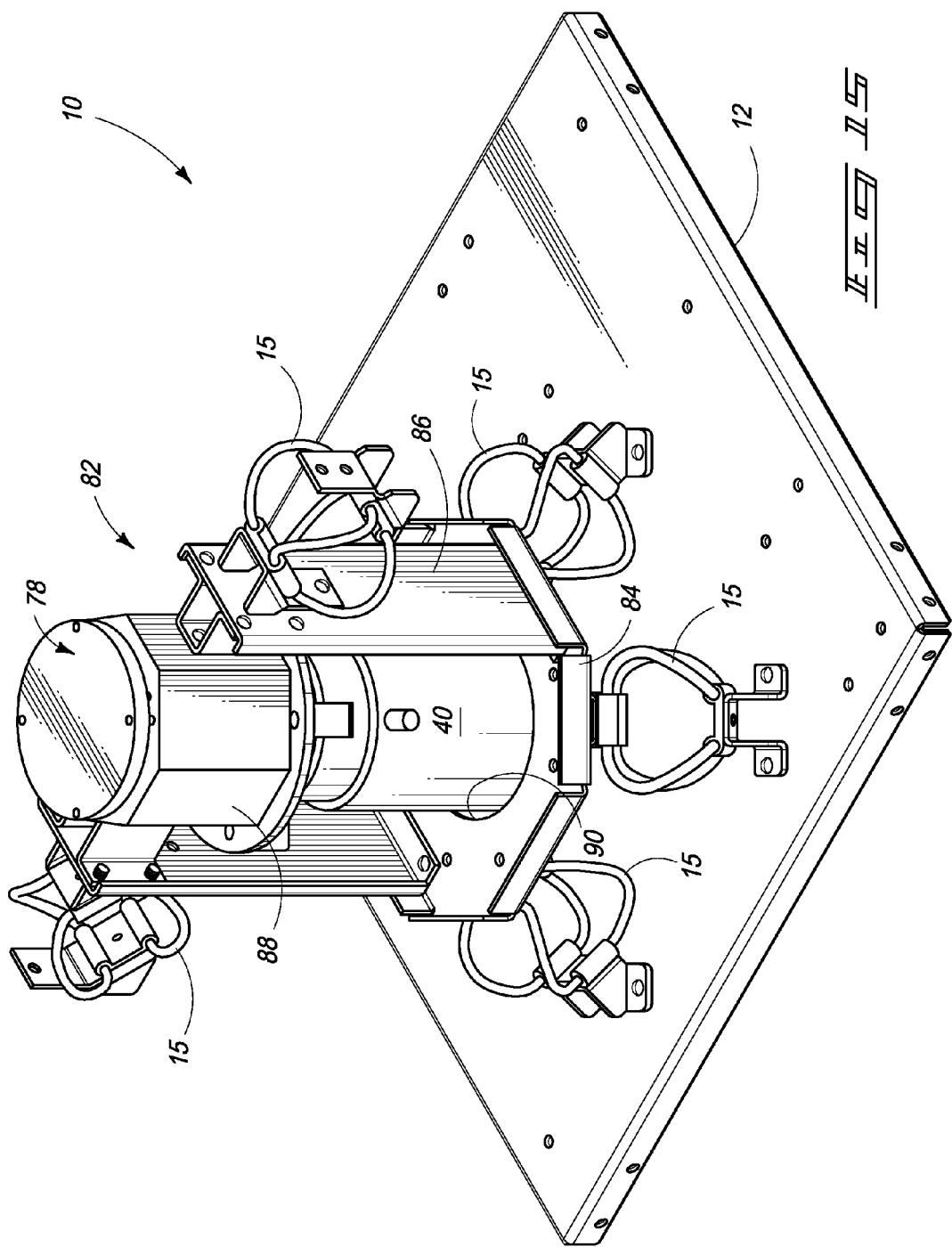
FIG. 15 is an isometric view of the instrument assembly of FIG. 13 according to an embodiment.

Referring to FIG. 15, an embodiment of instrument 10 is shown that includes housing 12 supporting a component isolation assembly 82 that is isolated from housing 12 by isolators 15. Component isolation assembly 82 can include a component isolation assembly base 84 as well as component isolation assembly sidewalls 86. Sidewalls 86 can extend vertically upward from base 84 and provide for attachment of isolators 15 to sidewalls 86. In the shown embodiment, component 78 can include an analyzer manifold 88 described in detail in PCT Application Serial No. PCT/US04/01144, filed Jan. 16, 2004, entitled Mass Spectrometer Assemblies, Mass Spectrometry Vacuum Chamber Lid Assemblies, and Mass Spectrometer Operational Methods, the entirety which is herein incorporated by reference. Analyzer manifold 88 can be connected to electronic components via wiring in an exemplary embodiment. Analyzer manifold can be coupled with vacuum component 40. In the exemplarily depicted embodiment, analyzer manifold 88 can be coupled to sidewalls 86 with component 40 extending through an opening 90 in base 84 of component isolation assembly 82. Component 40 can be in fluid connection via flexible tubing, in an exemplary embodiment, to a backing pump or rough pump (not shown).

Figure 16:
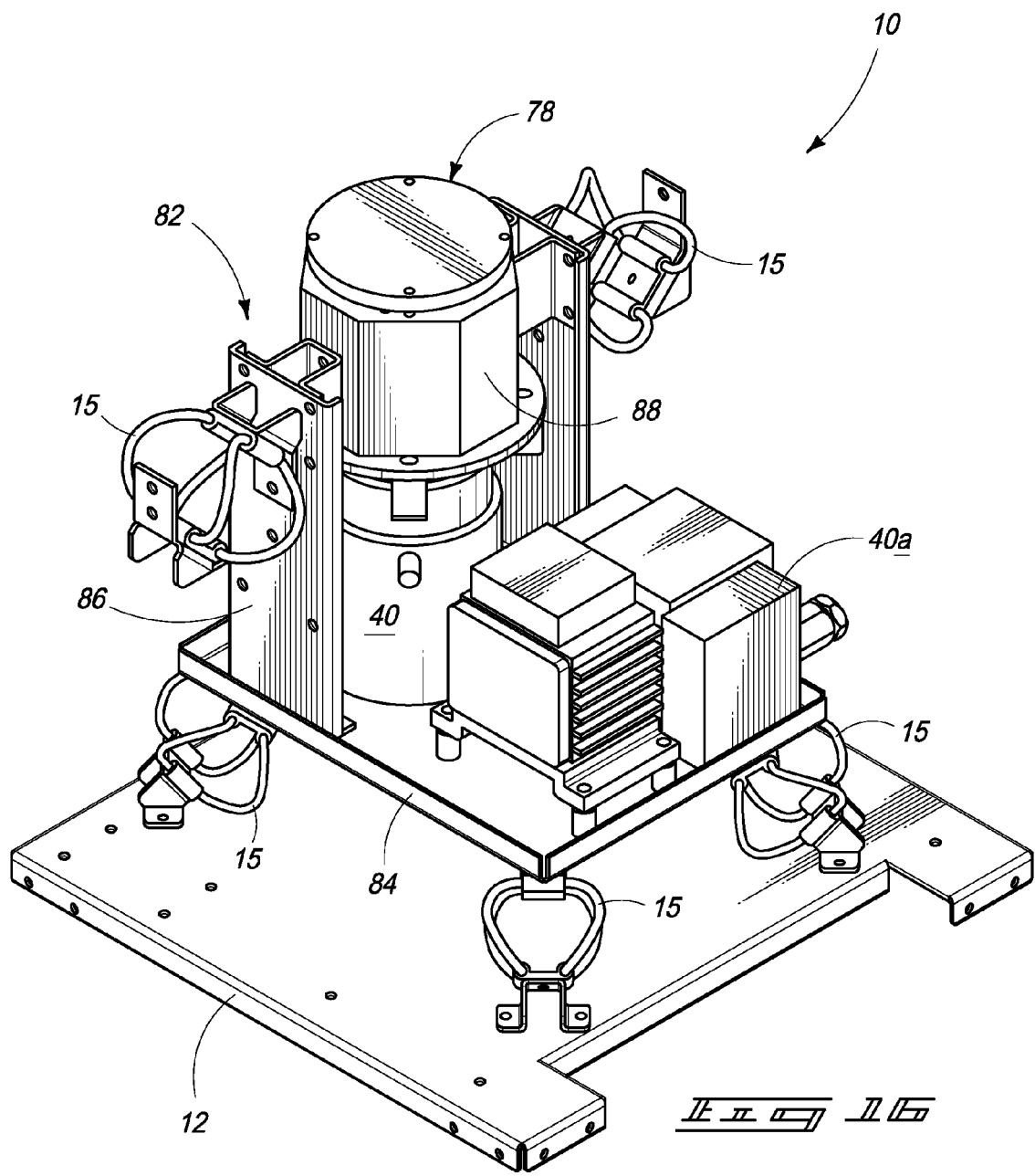
FIG. 16 is an isometric view of the instrument assembly of FIG. 13 according to an embodiment.

Referring next to FIG. 16, an embodiment of instrument 10 is shown that includes an embodiment of component isolation assembly 82. According to an embodiment, component isolation assembly 82 can include a component isolation assembly base 84 that supports sidewalls 86 and an additional vacuum component 40A, such as a backing pump. Component isolation assembly 82 can be rigidly affixed to components 78. As exemplarily depicted in FIG. 16 component isolation assembly 82 is rigidly affixed to analyzer manifold 88 and additional vacuum component 40A. In this configuration component 40 can be coupled with component 40A. As exemplary depicted in FIG. 16, component isolation assembly 82 can be isolated from housing 12 by at least four isolators 15 shown coupled to assembly base 84 proximate the bases corners and at least one additional isolator (not shown) coupled to about the center of base 84. In exemplary embodiments these additional isolators can be coupled to base 84 below component 40A.

Figure 17:
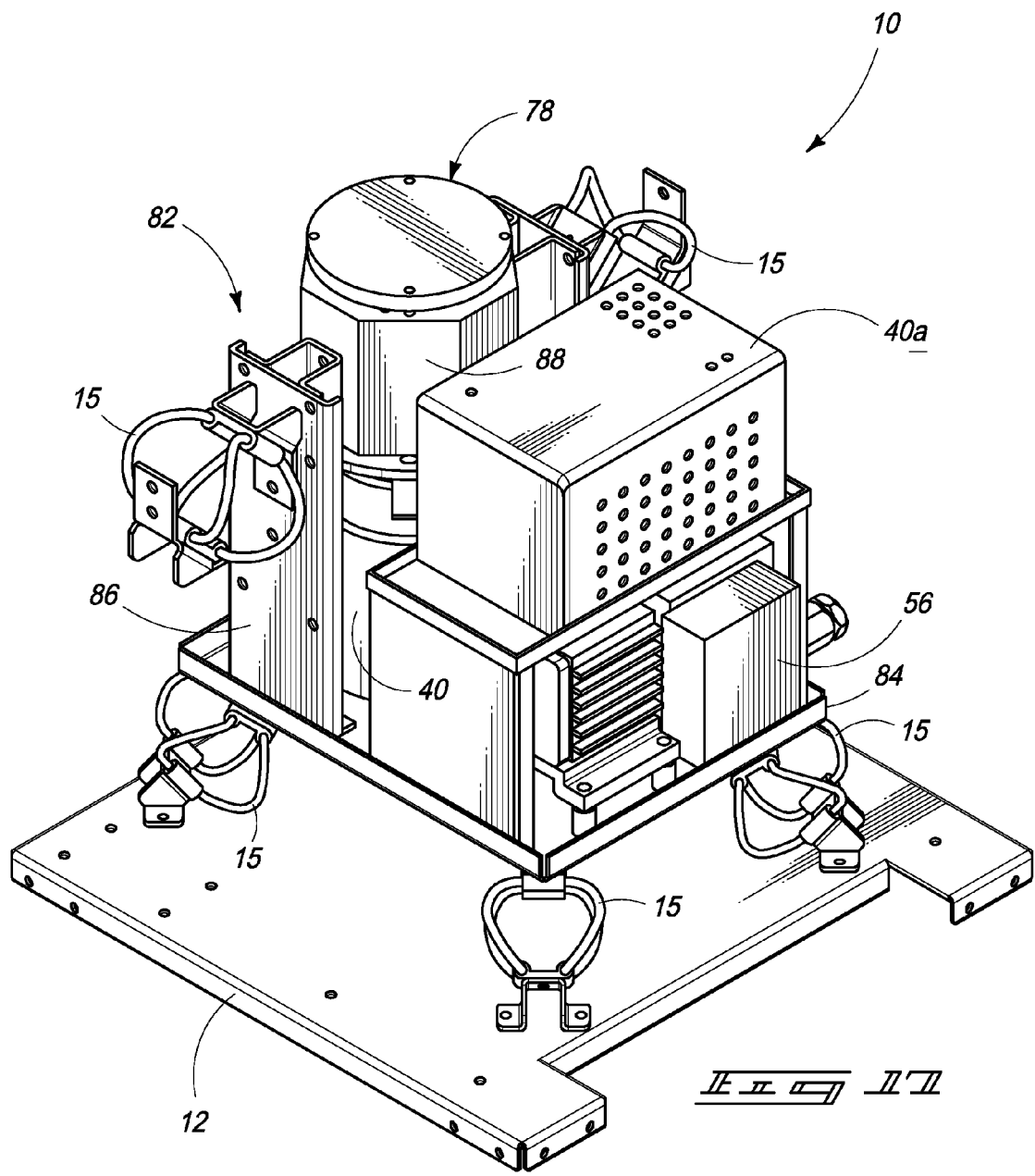
FIG. 17 is an isometric view of the instrument assembly of FIG. 13 according to an embodiment.

Referring next to FIG. 17, an embodiment of instrument 10 is shown that includes instrument housing 12 supporting isolators 15 that isolate an embodiment of component isolation assembly 82 from housing 12. Component isolation assembly 82 includes a base 84 and sidewalls 86 that can be rigidly affixed to and/or support components 78. In the exemplarily depicted embodiment, component isolation assembly 82 is rigidly affixed to and/or supports analyzer manifold 88, component 40A, and circuitry 56. As exemplarily depicted, circuitry 56 can be coupled to analyzer manifold 88 via cables, for example. While the depicted embodiments demonstrate the isolation of analysis components that include the analyzer manifold 88, components 40 and 40A, as well as circuitry 56, any combination of components 14 can be isolated according to the systems and methods described herein. For example, any and all the components described above may be mounted as described, to the exclusion of other components that may be rigidly affixed to housing 12. Further, components 78 may be individually isolated with each desired component having affixed thereto its own isolator 15.

Figure 18:
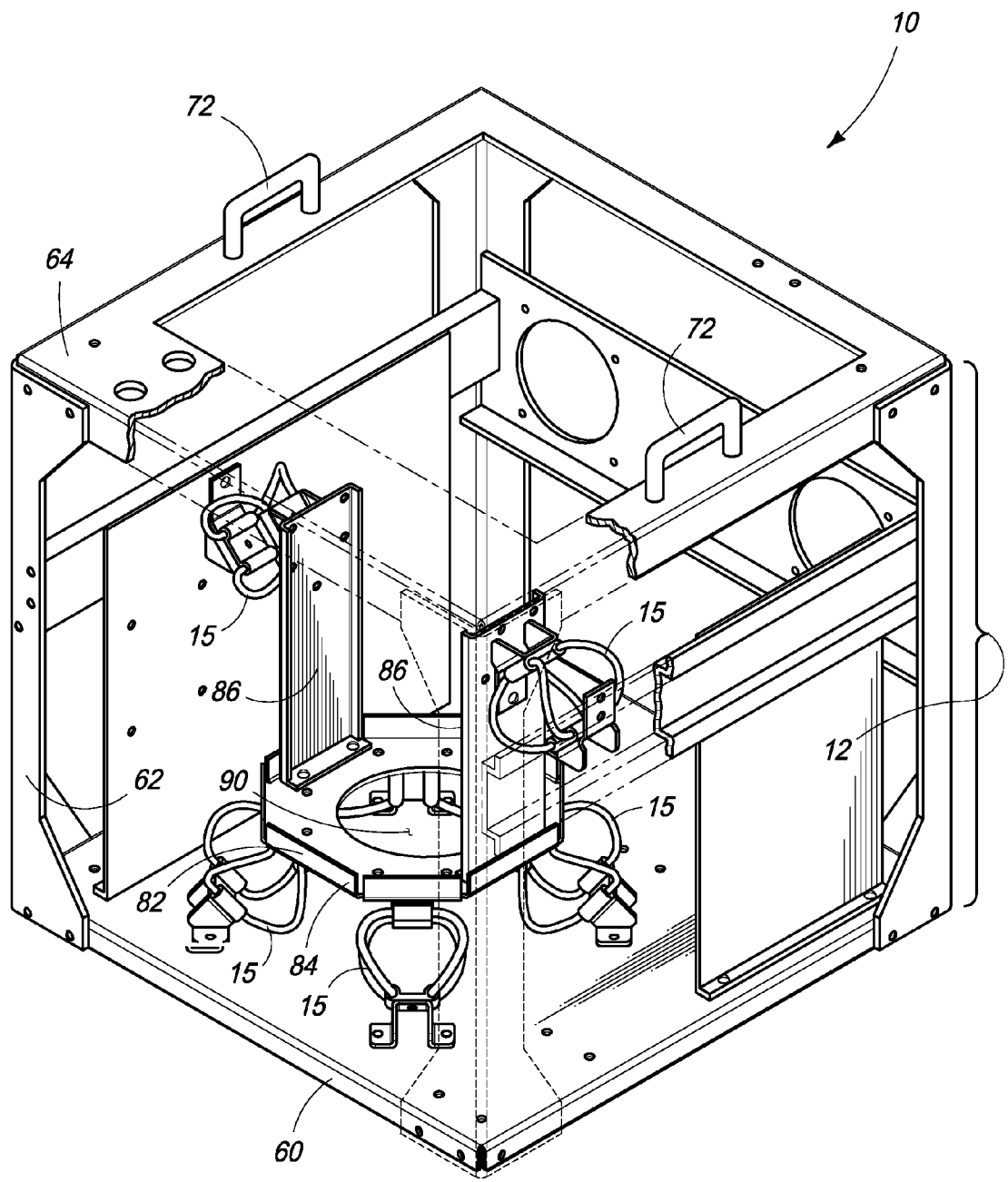
FIG. 18 is an isometric view of the instrument assembly of FIG. 13 according to an embodiment.

Referring next to FIG. 18, an exemplary embodiment of instrument 10 is shown that includes housing 12 at least partially encompassing a component isolation assembly 82. Housing 12 can include a base 60, supporting frame structure 62 extending upward, with a top or lid 64. In the shown embodiment of FIG. 18, top 64 can include handles 72. Component isolation assembly 82 can include a component isolation assembly base 84 and component isolation assembly sidewalls 86. Component isolation assembly base 84 can also include an opening 90. In exemplary embodiments, opening 90 can be configured to receive components 78 (not shown). Component isolation assembly 82 can be isolated from housing 12 by isolators 15. In the exemplarily depicted embodiment, isolators 15 can be placed along base 84 and along sidewalls 86. Isolators 15 can be affixed to housing 12 at points, for example, on frame 62 and base 60 of housing 12.

Figure 19:
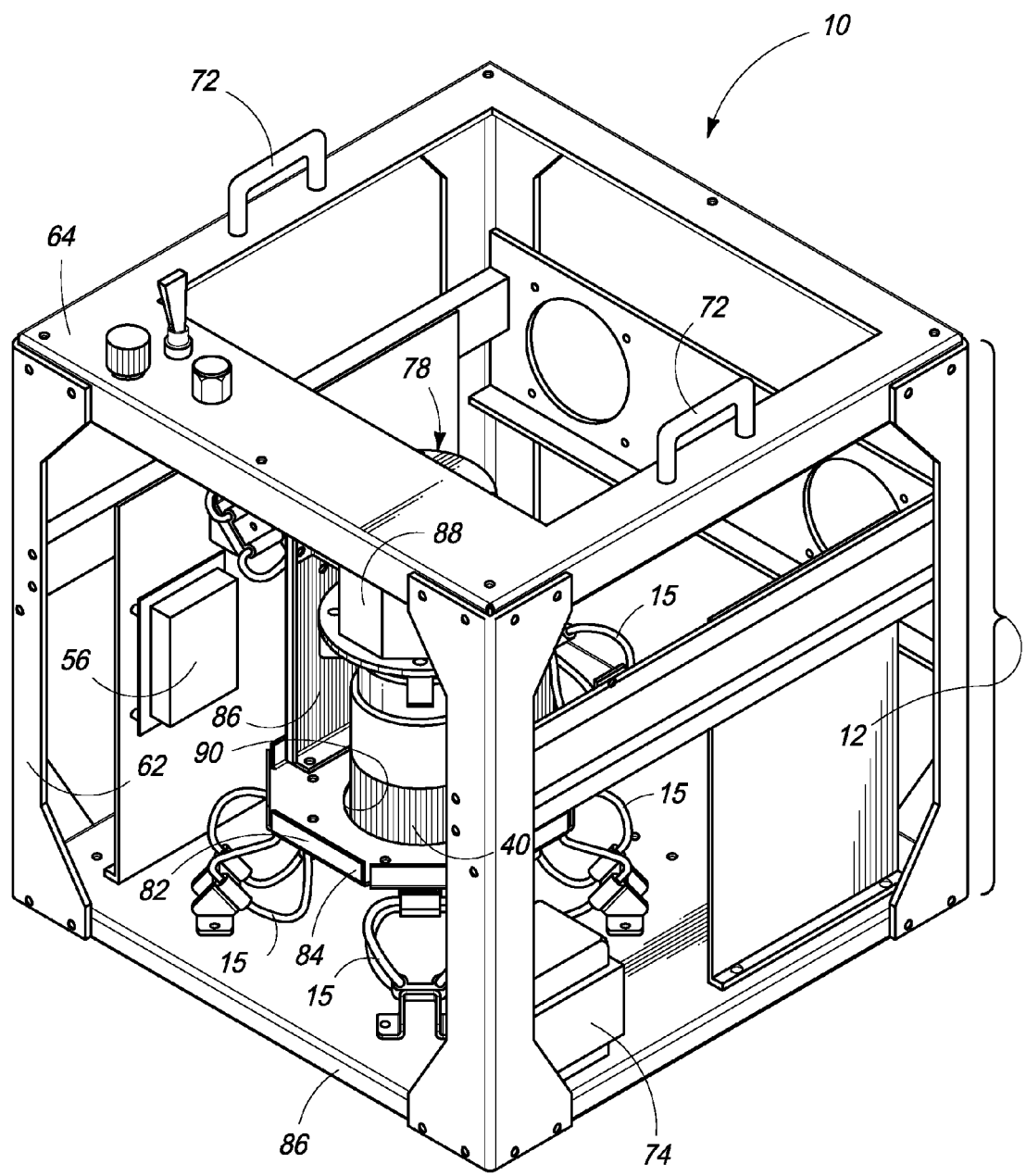
FIG. 19 is an isometric view of the instrument assembly of FIG. 13 according to an embodiment.

Referring next to FIG. 19, an embodiment of instrument 10 is shown with components 78 affixed to component isolation assembly. As described above, components 78 can include analyzer manifold 88 and vacuum component 40. In the shown exemplary embodiment of FIG. 19, circuitry 56 can be rigidly affixed to housing 12 while analyzer manifold 88 can be rigidly affixed to component isolation assembly 82 with vacuum component 40 extending through opening 90 of base 84. Exemplary circuitry 56 that can be rigidly affixed to housing 12 includes the RF circuitry of instrument 10.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

The invention claimed is:

1. A mass analysis instrument comprising:
a housing encompassing components of the instrument, the housing defining a space having a volume of equal to or less than about 100,000 cm$^3$, the components within the housing comprising:
a sample inlet component configured to one or both couple with at least one sampler external to the housing and/or receive sample directly;
a gas chromatography sample preparation component operatively coupled to the sample inlet component;
an ionization component operatively coupled to the gas chromatography sample preparation component;
an ion trap component operatively coupled to the ionization component, the ion trap component comprising a cylindrical ion trap or a linear ion trap;
an ion detection component operatively coupled to the ion trap component, the ion detection component comprising an electron multiplier having a conversion dynode;
a vacuum chamber housing at least the ionization component, the ion trap component and the ion detection component; and
a processing and control component operatively coupled to one or more of the inlet component, the sample preparation component, the ionization component, the ion trap component and/or the ion detection component.

2. The instrument of claim 1 wherein the sample inlet component comprises a syringe port, and wherein the sample inlet component is operatively configured to receive a sample and provide the sample to the sample preparation component.

3. The instrument of claim 1 wherein the instrument is configured to perform multidimensional mass analysis.

4. The instrument of claim 1 wherein the processing and control component is configured to provide mass analysis parameters to the ion trap component.

5. The instrument of claim 4 wherein the mass analysis parameters include waveforms.

6. The instrument of claim 1 wherein the inlet component is configured to receive gas phase samples directly into the inlet component when coupled to an external sampling device.

7. The instrument of claim 1 wherein the inlet component is configured to receive liquid phase samples directly into the inlet component when coupled to an external sampling device.

8. The instrument of claim 1 wherein the inlet component is configured to receive gas and liquid phase samples directly into the inlet component when coupled to an external sampling device.

9. The instrument of claim 1 wherein the inlet component is configured to receive gas, liquid, and solid phase samples directly into the inlet component.

10. The instrument of claim 1 wherein the inlet component is configured to sample air continuously.

11. The instrument of claim 1 wherein the ionization component is a chemical ionization component.

12. The instrument of claim 1 further comprising another ion trap component operatively aligned between the ionization component and the ion detection component.

13. The instrument of claim 1 wherein the ion detection component is configured to perform dual polarity ion detection.

14. A portable gas chromatography and mass analysis instrument comprising:
a sample inlet component;
a gas chromatography sample preparation component operatively coupled to the sample inlet component;
an ionization component operatively coupled to the gas chromatography sample preparation component;
an ion trap component operatively coupled to the ionization component;
an ion detection component operatively coupled to the ion trap component, the ion detection component comprising an electron multiplier having a conversion dynode;
a vacuum chamber housing at least the ionization component, the ion trap component and the ion detection component; and
a processing and control component operatively coupled to one or more of the sample inlet component, the sample preparation component, the ionization component, the ion trap component and/or the ion detection component.

15. The portable gas chromatography and mass analysis instrument of claim 14 wherein the components of claim 14 are confined within a housing defining a space having a volume of equal to or less than about 100,000 cm$^3$.

16. The portable gas chromatography and mass analysis instrument of claim 14 wherein the sample inlet component is configured to one or both couple with at least one sampler external to the housing and/or receive sample directly.

17. The portable gas chromatography and mass analysis instrument of claim 14 wherein the ion trap component comprises a cylindrical ion trap or a linear ion trap.

18. The portable gas chromatography and mass analysis instrument of claim 14 further comprising another ion trap component operatively aligned between the ionization component and the ion detection component.

* * * * *